US006288105B1

(12) United States Patent
Chirgadze et al.

(10) Patent No.: US 6,288,105 B1
(45) Date of Patent: Sep. 11, 2001

(54) ANTITHROMBOTIC AGENTS

(75) Inventors: Nickolay Y Chirgadze, Carmel; Matthew J Fisher, Mooresville; Richard W Harper, Indianapolis; Ho-Shen Lin, Indianapolis; Jefferson R McCowan, Indianapolis; Alan D Palkowitz, Carmel; Daniel J Sall, Greenwood; Gerald F Smith, Indianapolis; Kumiko Takeuchi, Indianapolis, all of IN (US); Minsheng Zhang, Warren, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/423,164

(22) PCT Filed: Apr. 30, 1998

(86) PCT No.: PCT/US98/08699
§ 371 Date: Feb. 3, 2000
§ 102(e) Date: Feb. 3, 2000

(87) PCT Pub. No.: WO98/48794
PCT Pub. Date: Nov. 5, 1998

Related U.S. Application Data

(60) Provisional application No. 60/045,163, filed on Apr. 30, 1997.

(51) Int. Cl.$^7$ .................. A61K 31/381; A61K 31/4025; C07D 409/10; C07D 409/12; A61P 7/02
(52) U.S. Cl. .................. 514/422; 514/233.5; 514/324; 514/337; 514/385; 514/443; 544/146; 546/202; 546/256; 546/281.1; 548/311.4; 548/525; 549/51; 549/58
(58) Field of Search .................. 548/525, 311.4; 546/202, 256, 281.1; 544/146; 549/51.58; 514/422, 443, 385, 337, 324, 233.5

(56) References Cited

U.S. PATENT DOCUMENTS

| 3,274,213 | 9/1966 | Lednicer . |
|---|---|---|
| 3,293,263 | 12/1966 | Lednicer . |
| 4,001,426 | 1/1977 | Brenner et al. . |
| 4,007,204 | 2/1977 | Descamps et al. . |
| 4,133,814 | 1/1979 | Jones et al. . |
| 4,418,068 | 11/1983 | Jones et al. . |
| 5,371,091 | 12/1994 | Misra et al. . |
| 5,441,965 | 8/1995 | Sall et al. . |
| 5,472,962 | 12/1995 | Koizumi et al. . |
| 5,510,357 | 4/1996 | Palkowitz . |
| 5,518,735 | 5/1996 | Sturzebecher et al. . |
| 5,523,309 | 6/1996 | Bryant et al. . |
| 5,532,254 | 7/1996 | Bowling . |
| 5,567,828 | 10/1996 | Dodge et al. . |
| 5,576,343 | 11/1996 | Nagahara et al. . |
| 6,025,382 | * 2/2000 | Bastian .................. 514/422 |

FOREIGN PATENT DOCUMENTS

| 0 617030 | 9/1994 | (EP) . |
|---|---|---|
| WO 95/10513 | 4/1995 | (WO) . |
| WO 95/17095 | 6/1995 | (WO) . |
| WO 95/17382 | 6/1995 | (WO) . |
| WO 96/11677 | 4/1996 | (WO) . |
| WO 97/25033 | 7/1997 | (WO) . |

OTHER PUBLICATIONS

Robert M. Scarborough, "Chapter 8. Anticoagulant Strategies Targeting Thrombin and Factor Xa," *Annual Reports in Medicinal Chemistry*, (1995) 30, pp. 71–80.
Jones, C., et al., *J. Med. Chem.*, 22 (8), 962–966 (1979).
Jones, C., et al., *J. Med. Chem*, 27 (8), 1057–1066 (1984).
Delgado and Remens, *Textbook of Organic Medicinal and Pharmaceutical Chemistry*, 9$^{th}$ Edition, 30–31 (1991).
Green and Wuts, *Protective Groups in Organic Syntnesis*, 2$^{nd}$ Edition, 77–79 (1991).
Bastian, et al., "Preparation of [(pyrrolidinoalkoxy) phenyl] benzothiophenes and analogs as thrombin inhibitors," *Chemical Abstracts*, vol. 127, No. 3 (1997).
Sall, et al., "Dibasic benzo[b]thiophene derivatives as a novel class of active site–directed thrombin inhibitors. 1. Determination of the serine protease selectivity, structure-activity relationships, and binding orientation, "*J. Med. Chem.*, vol. 40, No. 22, 24 Oct. 1997.

* cited by examiner

Primary Examiner—Evelyn Mei Huang
(74) Attorney, Agent, or Firm—Thomas E. Jackson; Arvie J. Anderson

(57) ABSTRACT

This application relates to novel compounds of formula I (and their pharmaceutically acceptable salts), as defined herein, processes and intermediates for their preparation, pharmaceutical formulations comprising the novel compounds of formula I, and the use of the compounds of formula I as thrombin inhibitors.

42 Claims, No Drawings

ANTITHROMBOTIC AGENTS

This application is a §371 of PCT/US98/08699, filed on Apr. 30, 1998, which international application claims priority from U.S. provisional application Serial No. 60/045,163, filed on Apr. 30, 1997.

This invention relates to thrombin inhibitors which are useful anticoagulants in mammals. In particular it relates to heterocyclic derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a method of inhibiting thrombin comprising using an effective amount of a thrombin inhibiting compound of formula I (or a pharmaceutically acceptable salt thereof)

I wherein
D is CH, $CR^d$ or N in which $R^d$ is methyl or methoxy;
E is CH, $CR^e$ or N in which $R^e$ is methyl, methoxy or halo;
$R^2$ is $-[X^2-(CH_2)_n]_p-N(R^a)-CO-A$ in which $X^2$ is a direct bond, methylene or O; n is 1, 2, 3 or 4; p is 0 or 1, $R^a$ is hydrogen or methyl; and —CO—A is a natural or unnatural α-amino acyl group, which may bear one or more pharmaceutically acceptable protecting groups and may be further substituted on the a-nitrogen, provided that p is 1 when —CO—A is a glycyl or N-substituted glycyl group; or —CO—A is 3-amino-4-hydroxy-1-oxobutyl;
$R^3$ is is $-X^3-(CH_2)_s-NR^sR^t$ or $-CH_2-R^k$, in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^k$ is 2-oxopyrrolidin-1-yl or 3-(1-oxoethyl)imidazolidin-1-yl; and
$R^6$ is hydrogen, hydroxy or methoxy.

A particular thrombin inhibiting compound of formula I (or a pharmaceutically acceptable salt thereof) is one wherein
D is CH, $CR^d$ or N in which $R^d$ is methyl or methoxy;
E is CH, $CR^e$ or N in which $R^e$ is methyl, methoxy or halo;
$R^2$ is $-[X^2-(CH_2)_n]p-N(R^a)-CO-A$ in which $X^2$ is a direct bond, methylene or O; n is 1, 2, 3 or 4; p is 0 or 1, $R^a$ is hydrogen or methyl; and —CO—A is a natural or unnatural α-amino acyl group, which may bear one or more pharmaceutically acceptable protecting groups and may be further substituted on the α-nitrogen, provided that p is 1 when —CO—A is a glycyl or N-substituted glycyl group;
$R^3$ is is $-X^3-(CH_2)_s-NR^sR^t$ or $-CH_2-R^k$, in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^k$ is 2-oxopyrrolidin-1-yl or 3-(1-oxoethyl)imidazolidin-1-yl; and
$R^6$ is hydrogen, hydroxy or methoxy.

The α-amino acyl group —CO—A conveniently may be represented as $-CO-CH(R^b)-NR^fR^g$, or may be denoted by standard amino acid nomenclature. Thus, —CO—A may be an α-amino acyl group derived from an α-amino acid selected from glycine, alanine, valine, leucine, isoleucine, phenylalanine, tyrosine, serine, threonine, methionine, cysteine, proline, azetidine-2-carboxylic acid, pipecolic acid, aspartic acid, asparginine, glutamic acid, glutamine, lysine, arginine, histidine, etc. in which an amino group may bear, for example, a t-butoxycarbonyl protecting group; a carboxy group may be protected as its (1–4C)alkyl ester; a hydroxy group may bear, for example, a benzyl protecting group; and a thiol group may bear, for example a t-butyl protecting group. In addition, when —CO—A is represented as —CO—CH($R^b$)—$NR^fR^g$, each of $R^f$ and $R^g$ may be hydrogen or methyl, or —$NR^fR^g$ may be a pyrrolidino, piperidino, morpholino or 1,1-dioxothiomorpholin-4-yl group (and $R^b$ denotes the side chain or protected side chain of an α-amino acyl group as defined above).

A particular value for D is CH.

A particular value for E is CH or $CR^e$ in which $R^e$ is methoxy.

A particular value for $R^3$ is pyrrolidinomethyl or 2-pyrrolidinoethoxy.

A particular value for —CO—A is O-benzyl-serinyl, L-serinyl, N-(t-butoxycarbonyl)-L-serinyl, L-aspartyl, L-phenylalanyl, L-alanyl, L-tyrosinyl, L-asparaginyl, N-(t-butoxycarbonyl)-γ-methyl-L-glutamyl or N-(t-butoxycarbonyl)-L-prolinyl.

Another particular value for —CO—A is (R)-3-amino-4-hydroxy-1-oxobutyl.

A particular value for $R^6$ is hydroxy.

When p is 1, a particular set of values is: $X^2$ is O and n is 2, 3 or 4.

A preferred value for p is 0.

One particular compound of formula I is the one described below as Example 2.

Another particular compound of formula I is the one described below as Example 17.

The present invention also provides a method of inhibiting coagulation in a mammal comprising administering to a mammal in need of treatment, a coagulation inhibiting dose of a thrombin inhibiting compound of formula I having any of the above definitions.

The present invention further provides a method of inhibiting thrombin comprising administering to a mammal in need of treatment, a thrombin inhibiting dose of a thrombin inhibiting compound of formula I having any of the above definitions.

Further, the present invention provides a method of treating a thromboembolic disorder comprising administering to a mammal in need of treatment, an effective dose of a thrombin inhibiting compound of formula I having any of the above definitions.

In addition, there is provided the use of a thrombin inhibiting compound of formula I having any of the above definitions for the manufacture of a medicament for treatment of a thromboembolic disorder.

As a further aspect of the invention, there is provided a prodrug (or a pharmaceutically acceptable salt thereof) of any of the above described thrombin inhibiting compounds of formula I which will form a prodrug. (It will be recognized that a thrombin inhibiting compound of formula I also may serve as a prodrug for a different thrombin inhibiting compound of formula I).

As an additional feature of the invention there is provided a pharmaceutical formulation comprising in association with a pharmaceutically acceptable carrier, diluent or excipient, a prodrug of a thrombin inhibiting compound of formula I (or of a pharmaceutically acceptable salt thereof) as provided in any of the above descriptions.

A compound of formula I in which —CO—A bears a protecting group may act directly as a thrombin inhibitor or indirectly as a result of its biotransformation to the corresponding compound of formula I without the protecting group.

In general, the thrombin inhibiting compounds of formula I are believed to be novel and, thus, to constitute an additional aspect of the invention. Thus, according to the invention there is provided a novel compound of formula I (or a pharmaceutically acceptable salt thereof) according to any of the above definitions of a compound of formula I, provided that the compound is not one which is not novel.

A pharmaceutically acceptable salt of an antithrombotic agent of the instant invention includes one which is an acid-addition salt made with an acid which provides a pharmaceutically acceptable anion or one which is the salt made with a base which provides a pharmaceutically acceptable cation. Thus, such a salt provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the above descriptions.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or transisomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–3C)alkyl group is methyl, ethyl, propyl or isopropyl; and for a (1–4C)alkyl group is methyl, ethyl, propyl, isopropyl or t-butyl.

A compound of formula I may be made by processes which include processes known in the chemical art for the production of known compounds of formula I or of structurally analogous compounds or by a novel process described herein. A process for a novel compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

In general, a compound of formula I may be prepared according to one of the routes outlined in Scheme I, and described in the examples, in which each of $Q^2$, $Q^3$ and $Q^6$, resectively, represents a value defined for the groups $R^2$, $R^3$ and $R^6$, a protected version of such a group, or moiety which can be further elaborated into such a group. Final conversion of a group $Q^2$, $Q^3$ or $Q^6$ into $R^2$, $R^3$ or $R^6$ is carried out at a convenient point, consistent with the chemistry employed. It will be recognized that a number of other routes may be used, particularly those involving condensation of an organometallic species to form a compound of formula C or G in Scheme I.

acylation of the amino group of a corresponding amine of formula II;

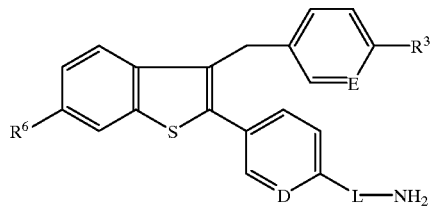

II

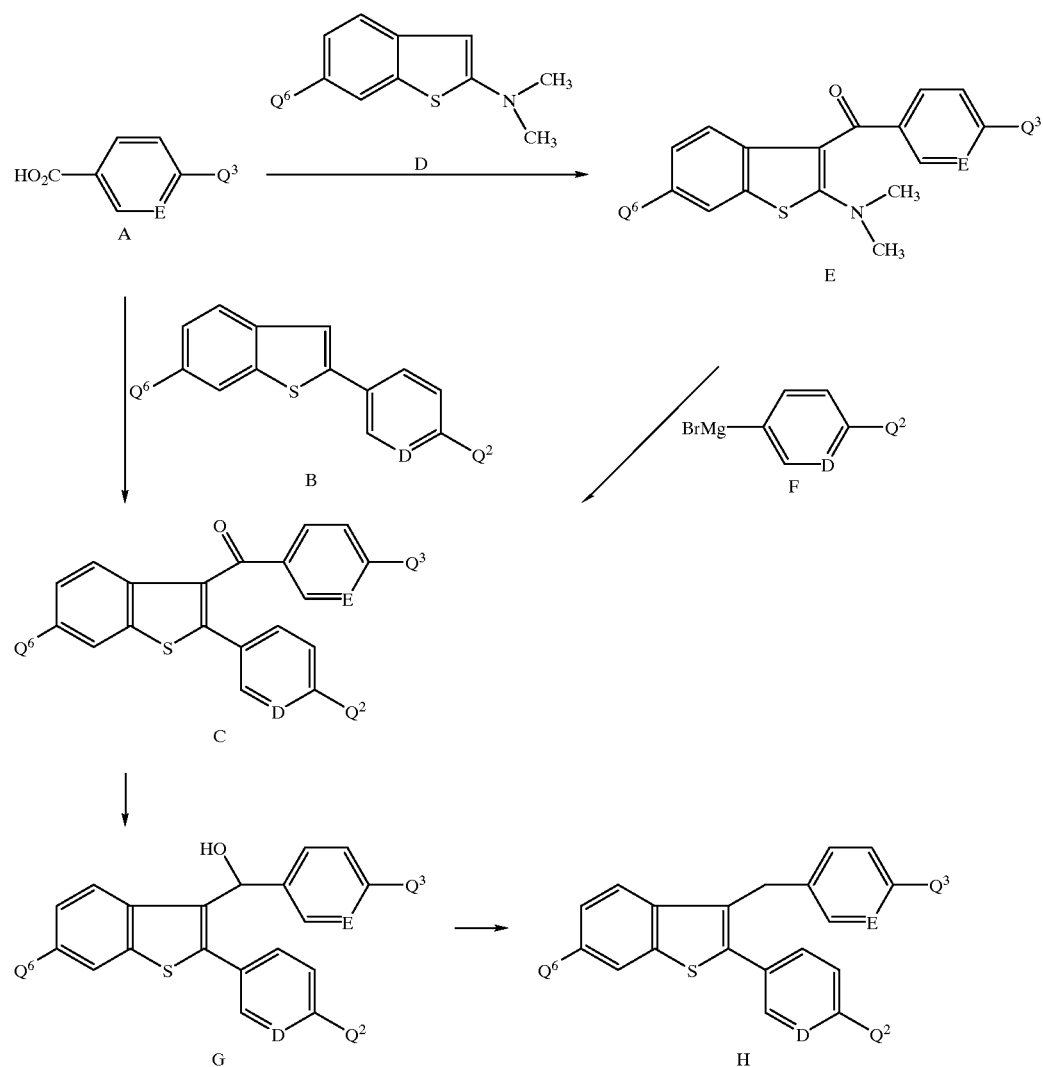

Scheme I

Thus, there is provided a process for preparing a novel compound of formula I (or a pharmaceutically acceptable salt thereof) as provided in any of the above descriptions which is selected from any of those described in the examples, including, wherein L is $[X^2\text{—}(CH_2)_n]_p$— with an acid of formula HO—CO—A, or an activated derivative thereof;

whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic or acidic form of such a compound of formula I with an acid or base affording a physiologically acceptable counterion or by any other conventional procedure.

An activated derivative of a carboxylic acid includes, for example, an ester (such as a methyl ester), an acid halide (such as an acid chloride), an activated ester (such as with 1-hydroxy-7-azabenzotriazole 1-hydroxybenzotriazole or N-hydroxysuccinimide), an anhydride with a carboxylic acid (such as by formed by reaction with butyl chloroformate) or an activated derivative formed by reaction with a coupling reagent (such as with a carbodiimide, for example with dicyclohexylcarbodiimide or with 1-(3-dimethyaminopropyl)-3-ethylcarbodiimide).

Novel intermediate or starting material compounds provide a further aspect of the invention.

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above in which $R^6$ which is hydroxy, but in which the corresponding substituent is —$OR^P$ in place of hydroxy, wherein $R^P$ is a phenol protecting group other than methyl. Phenol protecting groups are well known in the art, for example as described in T. W. Greene and P. G. M. Wuts, "Protecting Groups in Organic Synthesis" (1991). Particular values of $R^P$ include, for example, benzyl and allyl. Further, $R^P$ may denote a functionalized resin, for example as disclosed in H. V. Meyers, et al., *Molecular Diversity*, (1995), 1, 13–20.

As mentioned above, the invention includes pharmaceutically acceptable salts of the thrombin inhibiting compounds defined by the above formula I. A compound of formula I which bears an acidic moiety forms salts with pharmaceutically acceptable bases. Such a pharmaceutically acceptable salt may be made with a base which affords a pharmaceutically acceptable cation, which includes alkalai metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine. The potassium and sodium salt forms are particularly preferred.

A particular compound of of formula I which possesses one or more sufficiently basic functional groups to react with any of a number of inorganic and organic acids affording a physiologically acceptable counterion forms a pharmaceutically acceptable acid addition salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of protection and deprotection are well known in the art for preparation of compounds such as those corresponding to a compound of formula I, but in which $R^6$ is $OR^P$, discussed above. Selective methods for cleavage of methyl ethers, as described in the examples, are discussed in Jones, et al., *J. Med. Chem.*, (1984), 27, 1057–1066. For example, the diether 3-(4-methoxybenzoyl)- 2-(4-methoxyphenyl)benzo[b]thiophene may be treated with boron tribromide in dichloromethane at −10° C. (1 hour) to afford the monoether 2-(4-hydroxyphenyl)-3-(4-methoxybenzoyl)benzo[b]thiophene, whereas treatment with sodium thioethoxide affords the isomeric monoether 3-(4-hydroxybenzoyl)-2-(4-methoxyphenyl)benzo[b]thiophene. Treatment with boron tribromide under less mild conditions (0°, 6 hours) or with aluminum chloride and ethanethiol cleaves both ethers.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis).

Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |

-continued

| | |
|---|---|
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 µL buffer (0.03M Tris, 0.15M NaCl, pH 7.4) with 25 µL of human thrombin solution (purified human thrombin, Enzyme Research Laboratories, South Bend, Indiana, at 8 NIH units/mL) and 25 µl of test compound in a solvent (50% aqueous methanol (v:v)). Then 150 µL of an aqueous solution of the chromogenic substrate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$\text{Thrombin} + I \rightleftharpoons \text{Thrombin} - I$$

$$\text{Kass} = \frac{[\text{Thrombin-}I]}{[(\text{Thrombin}) \times (I)]}$$

Kass is calculated for a range of concentrations of test compounds and the mean value reported in units of liter per mole. In general, a thrombin inhibiting compound of formula I of the instant invention exhibits a Kass of $0.05 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 μg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982). In this model preferred compounds of the instant invention reduce the net clot weight to approximately 25–30% of control, or even lower, at an i.v. dose of 33.176 μmol/kg/h.

$FeCl_3$ Model of Arterial Injury

The carotid arteries are isolated via a midline ventral cervical incision A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Spontaneous Thrombolysis Model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}I$ human Fibrogen (5 μCi, ICN), immediately drawn into silastic tubing and incubated at 37° C. for 1 hour. The aged thrombus is expelled from the tubing, cut into 1 cm segments, washed 3X× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected } cpm - \text{lung } cpm)}{\text{injected } cpm} \times 100$$

The fibrinolytic dissolution of the implanted clot occurs time-dependently (see J. P. Clozel, *Cardiovas. Pharmacol.*, 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\ po}{AUC\ iv} \times \frac{Dose\ iv}{Dose\ po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means+/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model.

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle.

A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples and Preparations of representative intermediate compounds are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
Bn or Bzl=benzyl
Boc=tert-butoxycarbonyl
Bu=butyl
n-BuLi=butyllithium
calcd=calculated
DCC=dicyclohexylcarbodiimide
DIBAL-H=diisobutyl aluminum hydride
DMF=dimethylformamide
DMSO=dimethylsulfoxide
Et=ethyl
EtOAc=ethyl acetate
Et$_3$N=triethylamine
Et$_2$O=diethyl ether
EtOH=ethanol
EtSH=ethanethiol
FAB=Fast Atom Bombardment (Mass Spectrascopy)
FDMS=field desorption mass spectrum
Hex=hexanes
HOAt=1-hydroxy-7-azabenzotriazole
HPLC=High Performance Liquid Chromatography
HRMS=high resolution mass spectrum
i-PrOH=isopropanol
IR=Infrared Spectrum
LAH=lithium aluminum hydride
Me=methyl
MeI=methyl iodide
MeOH=methanol
MPLC=Medium Pressure Liquid Chromatography
NBS=N-bromosuccinimide
NMR=Nuclear Magnetic Resonance
Ph=phenyl
PPA=polyphosphoric acid
i-Pr=isopropyl Rochelle's Salt=potassium sodium tartrate
RPHPLC=Reversed Phase High Performance Liquid Chromatography
SiO$_2$=silica gel
SM=starting material
TBS=tert-butyldimethylsilyl
TEA=triethylamine
Temp.=temperature
TFA=trifluoroacetic acid
THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (™)" silica cartridges; radial chromatography indicates preparative chromatography using a "Chromatotron (™)" instrument.

PREPARATION 1

Preparation of 3-Methyl-4-[(1-pyrrolidinyl)methyl] phenyl 6-Methoxy-2-(4-aminophenyl)benzo[b] thiophen-3-yl Ketone

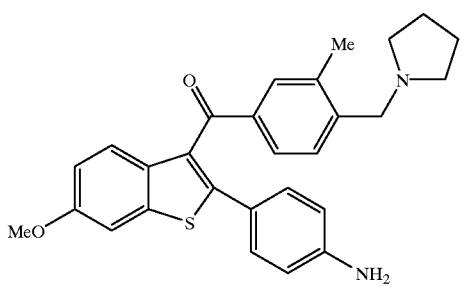

A. Methyl 3-Bromo-4-[(1-pyrrolidinyl)methyl]benzoate.

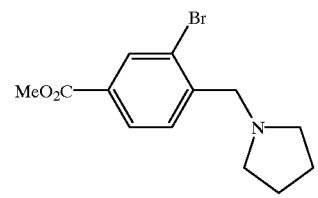

AIBN (79 mg, 48.0 mmol) was added to a stirred suspension of methyl 3-bromo-4-methylbenzoate (11.0 g, 48.0 mmol) and NBS (10.3 g, 57.6 mmol) in CCl$_4$ (400 mL), and the resultant mixture was heated to reflux for 2 h. After cooling to room temperature, the mixture was diluted with hexanes (200 mL) before it was filtered and concentrated to give 14.7 g (crude yield 100%) of methyl 3-bromo-4-(bromomethyl)benzoate.

Part of the crude dibromide (14.7 g) was dissolved in anhydrous CH$_2$Cl$_2$ (60 mL). The solution was cooled to 0° C. and treated with pyrrolidine (9.96 mL, 119 mmol), then it was allowed to stir at room temperature for 2 h. The reaction mixture was diluted with EtOAc (500 mL), washed with half-saturated aqueous NaHCO$_3$ (100 mL), dried over MgSO$_4$, filtered, and concentrated to give an oily residue. The crude product was chromatographed on silica [gradient 0–10% EtOH/Et$_3$N (2/1) in THF/hexanes (1/1)] to provide 6.45 g of the pyrrolidinyl ester (45%) as an oil.

IR (neat) 2953, 1728, 1602 cm$^{-1}$; $^1$H NMR (CDCl$_3$) δ 1.82 (br s, 4H), 2.61 (br s, 4H), 3.77 (s, 2H), 3.92 (s, 3H), 7.59 (d, J=8.0 Hz, 1H), 7.95 (dd, J=8.0 and 1.4 Hz, 1H), 8.20 (d, J=1.4 Hz, 1H); FDMS m/e 297 (M$^+$, $^{79}$Br) and 299(M$^+$, $^{81}$Br).

B. Methyl 3-Methyl-4-[(1-pyrrolidinyl)methyl]benzoate.

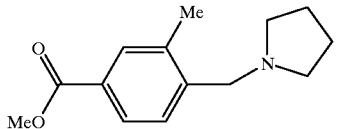

A solution of methyl 3-bromo-4-[(1-pyrrolidinyl)methyl] benzoate (16 g, 53.7 mmol) in 110 mL of toluene was treated with Pd(PPh$_3$)$_4$ (3.1 g, 2.68 mmol) and tetramethyltin (22.3 mL, 161.1 mmol). The resulting mixture was heated at 135–140° C. for 36 hr in a sealed tube. After cooling to ambient temperature, the reaction mixture was filtered through diatomaceous earth and concentrated in vacuo. The crude brown residue was purified by PrepLC (SiO$_2$; 97:2:1 hexanes-THF-TEA) to afford 11.4 g (48.9 mmol; 91%) of the title compound as a slightly yellow oil.

FDMS 233 (M$^+$); Anal. calcd for C$_{14}$H$_{19}$NO$_2$: C, 72.08; H, 8.21; N, 6.00. Found: C, 72.29; H, 8.17; N, 5.91.

C. 3-Methyl-4-[(1-pyrrolidinyl)methyl]benzoic Acid Hydrochloride.

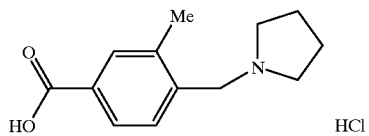

A solution of methyl 3-methyl-4-[(1-pyrrolidinyl)methyl] benzoate (16 g, 68.6 mol) in 250 mL of 1 N HCl was heated at reflux overnight (13 hr). After cooling to ambient temperature, the aqueous solution was extracted with EtOAc (150 mL). The aqueous layer was concentrated to give 16.8 g (65.7 mmol; 96%) of the title acid as a white solid.

FDMS 219 (M$^+$); Anal. calcd for C$_{13}$H$_{17}$NO$_2$.HCl: C, 61.06; H, 6.70; N, 5.48. Found: C, 61.22; H, 6.93; N, 5.37.

D. 6-Methoxybenzo[b]thiophene-2-boronic Acid.

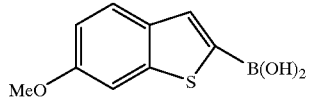

To a solution of 6-methoxybenzo[b]thiophene (Graham, S. L., et al. *J. Med. Chem.* 1989, 32, 2548–2554)(18.13 g, 0.111 mol) in 150 mL of anhydrous THF at −60° C. was added n-BuLi (76.2 mL, 0.122 mol, 1.6 M solution in hexanes), dropwise via syringe. After stirring for 30 min, triisopropyl borate (28.2 mL, 0.122 mol) was introduced via syringe. The resulting mixture was allowed to gradually warm to 0° C. and then partitioned between 1.0 N HCl and EtOAc (300 mL each). The layers were separated, and the organic phase was dried over Na$_2$SO$_4$. Concentration in vacuo produced a white solid that was triturated from Et$_2$O/hexanes. Filtration provided 16.4 g (71%) of 6-methoxybenzo[b]thiophene-2-boronic acid as a white solid.

mp 200° C. (dec); FDMS 208 (M$^+$; 100); $^1$H NMR (DMSO-d$_6$) δ 8.36 (br s), 7.86–7.75 (m, 2H), 7.53 (dd, J=8.1 and 2.0 Hz, 1H), 6.98 (m, 1H), 3.82 (s, 3H).

E. 6-Methoxy-2-(4-nitrophenyl)benzo[b]thiophene.

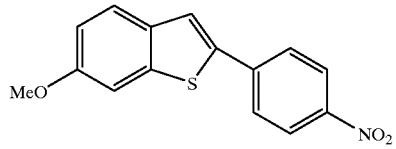

A solution of 15.0 g (71.8 mmol) of 6-methoxybenzo[b] thiophene-2-boronic acid (15.0 g, 74.3 mmol) of 1-bromo-4-nitrobenzene, and 1.50 mg (1.30 mmol) of tetrakis (triphenylphosphine)palladium(0) in 250 mL of THF was treated with 75 mL of 2 M aq Na$_2$CO$_3$. The mixture was protected from light and was heated to reflux for 16 h. The reaction was cooled to room temperature and was diluted with 200 mL of THF to effect solution. The two layers were separated and the organic layer was washed sequentially with 1 N aq NaOH (200 mL), H$_2$O (200 mL), and brine (200 mL). The organic phase was dried (Na$_2$SO$_4$), filtered and concentrated in vacuo to give 24.6 g of a yellow solid. Recrystallization from EtOAc afforded 18.6 g (65.1 mmol; 91%) of the title compound as yellow crystals.

FDMS 285 (M$^+$); Anal. calcd for C$_{15}$H$_{11}$NO$_3$S: C, 63.15; H, 3.89; N, 4.91. Found: C, 63.38; H, 4.01; N, 4.81.

F. 6-Methoxy-2-(4-aminophenyl)benzo[b]thiophene.

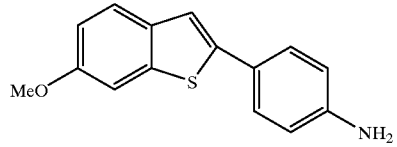

A solution of 9.00 g (31.5 mmol) of 6-methoxy-2-(4-nitrophenyl)benzo[b]thiophene (Part A) in 250 mL of EtOAc was treated with 1.0 g of 10% Pd—C which had been prewetted with the same solvent. The mixture was hydrogenated at 4.1 bar until hydrogen consumption had ceased. The reaction was filtered, concentrated in vacuo, and the resulting solid recrystallized from EtOAc to give 7.90 g (30.9 mmol; 98%) of the title compound as a solid.

FDMS 255 (M+).

G. 6-Methoxy-2-(4-acetamidophenyl)benzo[b]thiophene.

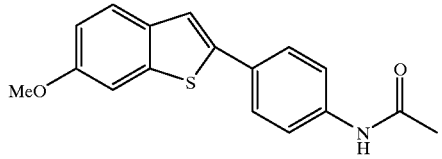

A solution of 15.0 g (58.7 mmol) of 6-methoxy-2-(4-aminophenyl)benzo[b]thiophene (Part B) in 350 mL of pyridine was treated with 17.0 mL (180 mmol) of acetic anhydride in a dropwise manner. After stirring for 2 h, the reaction was concentrated in vacuo to give 15.1 g (50.7 mmol; 87%) of the title compound as a yellow solid.

FDMS 297 (M+); Anal. calcd for C$_{17}$H$_{15}$NO$_2$S: C, 68.66; H, 5.08; N, 4.71. Found: C, 68.44; H, 5.05; N, 4.64.

H. 3-Methyl-4-[(1-pyrrolidinyl)methyl]phenyl 6-methoxy-2-(4-acetamidophenyl)benzo[b]thiophen-3-yl Ketone.

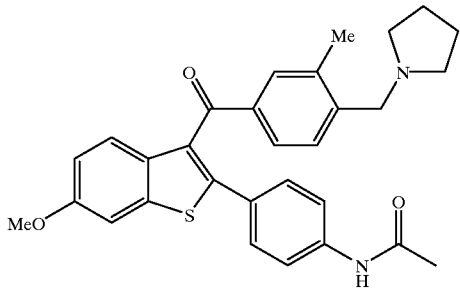

A slurry of 1.25 g (4.89 mmol) of 3-methyl-4-[(1-pyrrolidinyl)methyl]benzoic acid hydrochloride in 50 mL of dichloroethane was treated with 2 drops of DMF followed by 1.30 mL (14.9 mmol) of oxalyl chloride. The reaction was stirred at ambient temperature until gas evolution ceased and was concentrated in vacuo. The solid was reconstituted in 50 mL dichloroethane. The mixture was cooled to 0° C., was treated with 1.30 g (4.37 mmol) of 6-methoxy-2-(4-acetamidophenyl)benzo[b]thiophene and 2.60 g (19.5 mmol) of AlCl$_3$, and was stirred at ambient temperature for 5 h. The reaction was quenched by the addition of 100 mL of sat'd aq NaHCO$_3$. The two layers were separated and the aqueous layer was extracted with EtOAc (4×50 mL). The combined organic layers were washed with H$_2$O (100 mL), dried (K$_2$CO$_3$), filtered, and concentrated in vacuo to give 1.30 g of a yellow foam. Flash chromatography (SiO$_2$; 5% MEOH in CHCl$_3$ sat'd with NH$_4$OH) afforded 730 mg (1.46 mmol; 30%) of the title compound as a foam.

FDMS 498 (M+); Anal. calcd for C$_{30}$H$_{30}$N$_2$O$_3$S: C, 72.26; H, 6.06; N, 5.62. Found: C, 72.20; H, 6.31; N, 5.79.

I. 3-Methyl-4-[((1-pyrrolidinyl)methyl]phenyl 6-Methoxy-2-(4-aminophenyl)benzo[b]thiophen-3-yl Ketone.

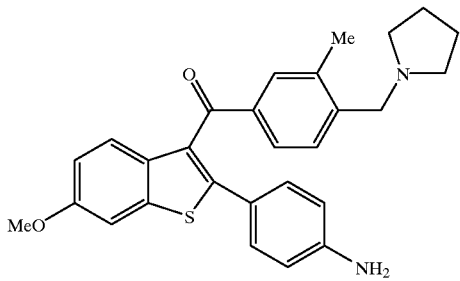

A solution of 200 mg (0.40 mmol) of 3-methyl-4-[(1-pyrrolidinyl)methyl]phenyl 6-methoxy-2-(4-acetamidophenyl)benzo[b]thiophen-3-yl ketone (Part H) in 5 mL of MEOH was treated with 5 mL of conc. aq HCl. The reaction was heated to mild reflux for 1 hr and was concentrated in vacuo. The residue was taken up in 25 mL. of H$_2$O, the solution basified to pH 12 with 5 N aq NaOH, and the mixture was extracted with EtOAc (2×25 mL). Trhe comrbined organic extracts were dried (K$_2$CO$_3$), filtered, and concentrated in vacuo to give 175 mg (0.38 mmol; 96%) of the title compound as a foam.

FDMS 456 (M+); Anal. calcd for C$_{28}$H$_{28}$N$_2$O$_2$S: C, 73.65; H, 6.18; N, 6.14. Found: C, 73.52; H, 6.17; N, 6.03.

PREPARATION 2

Preparation of 2-[4-(2-Aminoethoxy)phenyl]-3-[4-[2-(1-pyrrolidinyl)ethoxy]benzyl]benzo[b]thiophene Dihydrochloride

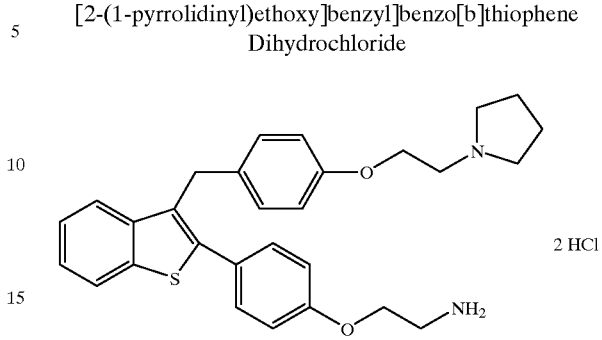

The 2-(4-hydroxyphenyl)-3-[4-[2-(1-pyrrolidinyl)ethoxy] benzyl]benzo[b]thiophene starting material for the above amine may be obtained by either of the methods described below.

A. 2-(4-Methoxyphenyl)benzo[b]thiophene.

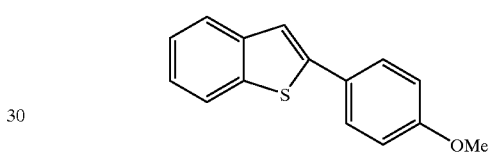

The title compound was prepared in 91% yield from benzo[b]thiophene-2-boronic acid and 4-bromoanisole by using a coupling procedure similar to that described above in Example 1, Part D.

mp 188–191° C.; $^1$H NMR (DMSO-d$_6$) δ 7.94 (d, J=8.0 Hz, 1H), 7.81 (d, J=7.0 Hz, 1H), 7.73 (m, 2H), 7.71 (s, 1H), 7.35 (m, 2H), 7.05 (d, J=8.0 Hz, 2H), 3.82 (s, 3H); FDMS 240 (M$^+$; 100); Anal. Calcd for C$_{21}$H$_{23}$NO$_2$S: C, 71.36; H, 6.56; N, 3.86. Found: C, 71.46; H, 6.60; N, 3.86.

B. 2-(4-Methoxyphenyl)benzo[b]thiophen-3-yl 4-[2-(1-Pyrrolidinyl)ethoxy]phenyl Ketone.

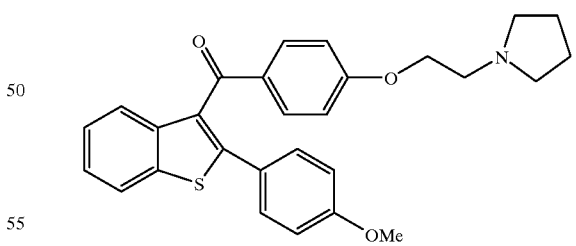

By converting 4-[2-(1-pyrrolidinyl)ethoxy]benzoic acid hydrochloride into the corresponding benzoyl chloride hydrochloride using thionyl chloride and catalytic DMF in refluxing dichloromethane to form the benzoyl choride, followed by acylation using AlCl$_3$ in 1,2-dichloroethane at 0° C., the title compound was prepared from 2-(4-methoxyphenyl)benzo[b]thiophene in 59% yield as an oil following radial chromatography (SiO$_2$; gradient of 2–5% MeOH in CH$_2$Cl$_2$).

C. 2-(4-Hydroxyphenyl)benzo[b]thiophen-3-yl 4-[2-(1-Pyrrolidinyl)ethoxy]phenyl Ketone.

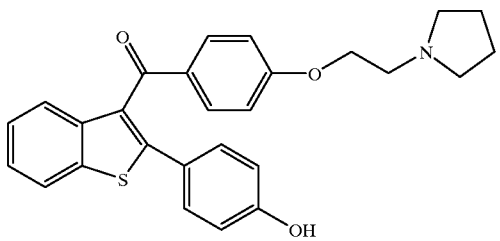

By cleaving the methyl ether of 2-(4-methoxyphenyl) benzo[b]thiophen-3-yl 4-[2-(1-pyrrolidinyl)ethoxy]phenyl ketone using $AlCl_3$ (about 8 eq) and EtSH (about 10 eq) in dichloroethane at 0° C., the title compound was obtained in 33% yield as an oil following radial chromatography ($SiO_2$; gradient of 2–10% MeOH in $CH_2Cl_2$).

FDMS 443 ($M^+$; 100); Anal. Calcd For $C_{27}H_{25}NO_3S$: C, 73.11; H, 5.68; N, 3.16. Found: C, 73.11; H, 5.89; N, 3.20.

D. 2-(4-Hydroxyphenyl)-3-[4-[2-(1-pyrrolidinyl)ethoxy] benzyl]benzo[b]thiophene.

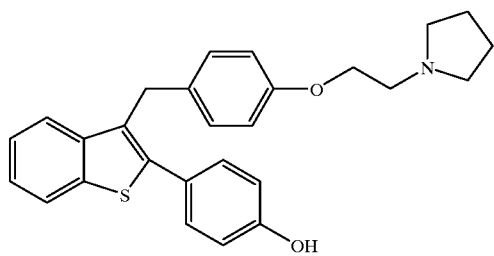

A 0° C. solution of 7.40 g (16.7 mmol) of 2-(4-hydroxyphenyl)benzo[b]thiophen-3-yl 4-[2-(1-pyrrolidinyl) ethoxy]phenyl ketone in 500 mL of THF was treated with 67.0 mL of a solution of DIBAL-H (1 N in toluene; 67 mmol). The reaction was stirred at 0° C. for 1 h and was quenched by the careful addition of 50 mL of MeOH. Saturated aq. sodium/potassium tartrate (200 mL) and EtOAc (200 mL) were added and the reaction stirred vigourously for 1 h. The two layers were separated and the aqueous layer was extracted with EtOAc (3×200 mL). The combined organic layers were dried ($K_2CO_3$), filtered and concentrated in vacuo. The residue was taken up in dichloroethane (300 mL). The solution was cooled to 0° C. and was treated with 20.0 mL (125 mmol) of triethylsilane followed by 13.0 mL (168 mmol) of trifluoroacetic acid. The reaction was stirred at 0° C. for 1 h and was poured into 250 mL of sat'd aq. $NaHCO_3$. The two layers were separated and the organic layer was dried ($K_2CO_3$), filtered, and concentrated in vacuo to give 6.53 g of a foam. Flash chromatography ($SiO_2$; 25% THF: 5% TEA: 70% hexanes) afforded 5.45 g (12.7 mmol; 76%) of the title compound as a foam.

$^1$H NMR (DMSO-$d_6$) d 9.77 (s, 1H), 7.90 (d, J=8.8 Hz, 1H), 7.93–7.87 (m, 1H), 7.32–7.24 (m, 4H), 6.97 (d, J=8.7 Hz, 2H), 6.86–6.75 (m, 4H), 4.13 (s, 2H), 3.97 (t, J=5.8 Hz, 2H), 2.87–2.78 (m, 2H), 2.61–2.52 (m, 4H), 1.69–1.61 (m, 4H).

E. 2-(4-Methoxyphenyl)benzo[b]thiophen-3-yl 4-[2-(1-Pyrrolidinyl)ethoxy]phenyl Ketone.

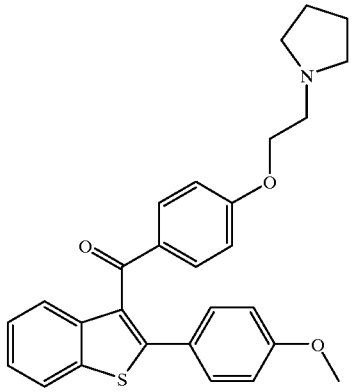

Sodium hydride (0.69 g of 60% NaH in mineral oil; 17.22 mMol) was suspended in 15 mL of dry DMF in a flame-dried, argon-filled flask. After stirring for 15 min, a solution of 4-(1-pyrrolidinyl)ethanol was added. After stirring for 15 min and gas evolution had ceased, 4-fluorophenyl 2-(4-methoxyphenyl)benzo[b]thiophen-3-yl ketone [prepared by acylation of 2-(4-methoxyphenyl)benzo[b]thiophene with 4-fluorobenzoyl chloride] (5.2 g; 14.34 mmol) in 15 mL of dry DMF was added. The mixture was stirred at room temperature for 5 h, then poured into 25 mL of water. Extraction was carried out with EtOAc (4×25 mL). The combined organics were washed with brine and dried by passage through sodium sulfate. The title compound (5.12 g; 78% yield) was isolated as a colorless oil by flash chromatography on silica gel, eluting with a gradient of EtOAc (100–85%)/$Et_3N$(0–5%)/MeOH(0–10%).

$^1$NMR (CDCl$_3$) δ 7.85 (m, 1H), 7.76 (d, J=6.3, 2H), 7.63 (m, 1H), 7.36 (m, 4H), 6.77 (d, J=7.2, 4H), 4.22 (t, J=5.3, 2H), 3.75 (s, 3H), 3.04 (t, J=5.2, 2H), 2.83 (br s, 4H), 1.90 (br s, 4H); FDMS 457 (M).

F. 2-(4-Methoxyphenyl)-3-[4-[2-(1-pyrrolidinyl)ethoxy] benzyl]benzo[b]thiophene.

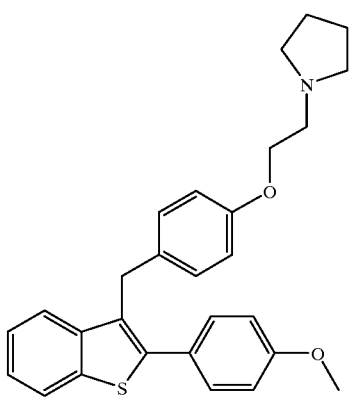

To the above ketone (Part E) Part I) (3.12 g; 11.2 mmol) in 40.0 mL of THF was added 0.42 g (11.2 mmol) of LAH at 0° C. The bath was removed and the mixture was stirred for 1 h. Hydrolysis was effected by addition of 0.42 mL of water, 0.42 mL of 5N NaOH, and 1.26 mL of water, followed by stirring for 1 h. After the mixture was filtered and washed with THF, the filtrate was concentrated; and the intermediate carbinol was dried in vacuo for 25 min. The carbinol was dissolved in methylene chloride (40.0 mL) under argon atmosphere and cooled in an ice-water bath. Triethylsilane (12.5 mL; 78.3 mmol) was added, followed by dropwise addition of 8.6 mL (112.0 mmol) of TFA. Upon completion of addition of TFA, the bath was removed and stirring was continued for 2 h. Saturated aqueous sodium bicarbonate (50 mL) was added, and extraction was carried out with EtOAc. The combined organics were washed with brine and dried by passage through sodium sulfate. The title compound (4.45 g; 90% yield) was isolated as a colorless oil by flash chromatography on silica gel, eluting with a gradient of EtOAc(100–95%)/Et$_3$N(0–5%).

$^1$NMR (CDCl$_3$) δ 7.87 (m, 1H), 7.77 (d, J=6.4, 2H), 7.65 (m, 1H), 7.34 (m, 4H), 6.78 (d, J=7.4, 4H), 4.20 (s, 2H), 4.15 (t, J=5.3, 2H), 3.73 (s, 3H), 3.14 (t, J=5.4, 2H), 2.91 (br s, 4H), 1.90 (br s, 4H); FDMS 444 (M+1).

G. 2-[4-Hydroxyphenyl]-3-[4-[2-(1-pyrrolidinyl)ethoxy]benzyl]benzo[b]thiophene.

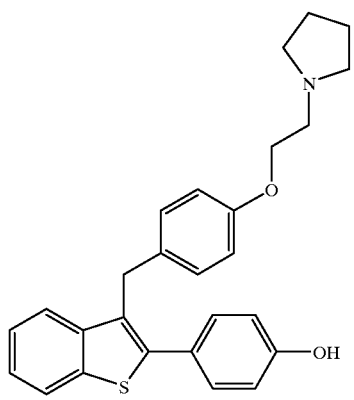

The above methyl ether (4.5 g; 10.1 mmol) (Part F) was dissolved in 45 mL of dichloroethane under an argon atmosphere and cooled in an ice-water bath. To this was added ethanethiol (6.0 mL; 81.1 mmol) and 5.41 g (40.6 mmol) of aluminum chloride, and the mixture was stirred in the cold bath for 1 h. Saturated NaHCO$_3$ was added, and stirring was continued while warming to room temperature for 1 h. The title compound (0.23 g; 74% yield) was isolated by filtration and washed with water.

$^1$NMR (CDCl$_3$) δ 7.83 (m, 1H), 7.47 (m, 1H), 7.29 (m, 2H), 6.98 (d, J=8.5, 2H), 6.83 (m, 4H), 6.69 (d, J=8.6, 2H), 4.15 (m, 4H), 3.05 (m, 2), 2.85 (br s, 4H), 1.91 (br s, 4H); FDMS 430 (M+1).

H. 2-[4-[2-(t-Butyloxycarbonylamino)ethoxy]phenyl]-3-[4-[2-(1-pyrrolidinyl)ethoxy]benzyl]benzo b]thiophene Oxalate.

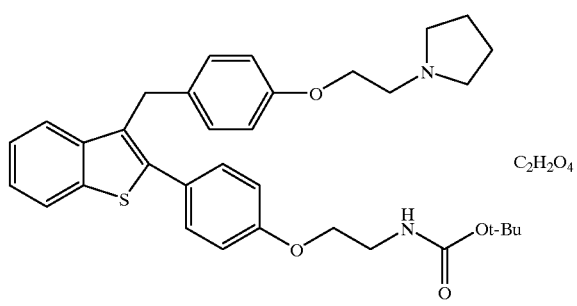

A mixture of 2.0 g (4.66 mmol) of 2-(4-hydroxyphenyl)-3-[4-[2-(1-pyrrolidinyl)ethoxy]benzyl]benzo[b]thiophene, 1.47 g (5.60 mmol) of triphenylphosphine, and 0.90 g (5.60 mmol) of N-t-Boc-aminoethanol in 20 mL of THF was cooled to 5° C. and was treated with 0.88 mL (5.60 mmol) of diethyl azodicarboxylate. The cooling bath was removed and the reaction stirred at ambient temperature for 23 hours. The mixture was diluted with 20 mL of saturated NaCl solution and the layers were separated. The organic layer was dried over K$_2$CO$_3$, filtered and concentrated in vacuo to afford 5.47 g of an oil. Purification by flash chromatrography (SiO$_2$; 2% then 5% MeOH in CHCl$_3$ saturated with NH$_4$OH) afforded 1.43 g (2.50 mmol; 54%) of the free base of the title compound as a foam. The product was converted to the oxalate salt by dissolving it in a minimal amount of MeOH and treament with an equimolar amount of oxalic acid, followed by isolation and drying of the resultant solid.

FDMS 487 (M+1); Anal. Calcd for C$_{34}$H$_{38}$N$_2$O$_{10}$S: C, 61.25; H, 5.75; N, 4.20. Found: C, 60.98; H, 5.66; N, 4.00.

I. 2-[4-(2-Aminoethoxy)phenyl]-3-[4-[2-(1-pyrrolidinyl)ethoxy]benzyl]benzo[b]thiophene Dihydrochloride.

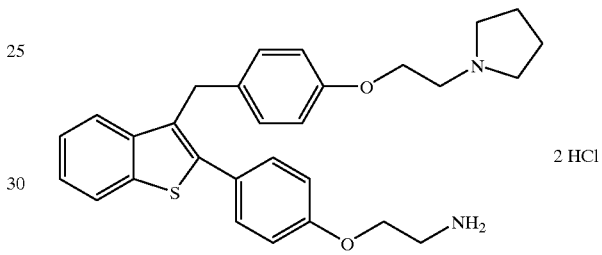

A solution of 1.20 g (2.10 mmol) of the above urethane (Part H) in 5.0 mL of anisole was treated with 10.0 mL of TFA. The reaction was stirred overnight and was concentrated in vacuo. The residue was partitioned between 50 mL of 1 N aq HCl and 50 mL of hexanes. The aqueous layer was separated, washed with hexanes (2×50 mL) and EtOAc (2×50 mL), and lyopholized to afford 964 mg (1.77 mmol; 84%) of the title compound.

FDMS 487 (M+1); Anal. Calcd for C$_{29}$H$_{32}$N$_2$O$_2$S. 2 HCl: C, 63.84; H, 6.28; N, 5.13. Found: C, 64.14; H, 6.33; N, 5.11.

PREPARATION 3

Preparation of 2-[4-(3-Aminopropoxy)phenyl]-3-[4-[2-(1-pyrrolidinyl)ethoxy]benzylbenzo[b]thiophene

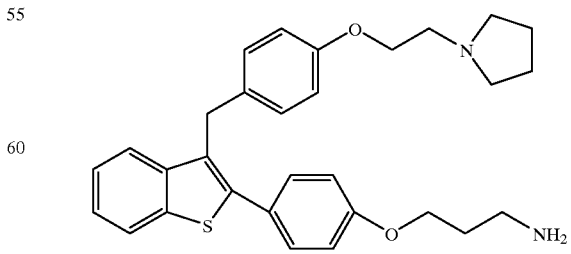

A. 2-[4-[3-(N-Phthalimidyl)propoxy]phenyl)-3-[4-[2-(1-pyrrolidinyl)ethoxy]benzylbenzo[b]thiophene.

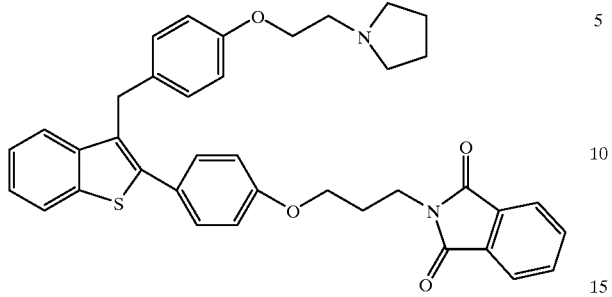

To 2-(4-hydroxyphenyl)-3-[4-[2-(1-pyrrolidinyl)ethoxy]benzyl]benzo[b]thiophene (Preparation 2, Part D or G; 51 mg, 0.116 mmol) in THF (1 mL) was added potassium hexamethyldisilazane (KHMDS) (0.5 M in toluene, 0.26 mL, 0.128 mmol) and the mixture stirred under $N_2$ for 30 min. N-(3-Bromopropyl)phthalimide (31 mg, 0.116 mmol) in THF (1 mL) and a catalytic amount of $Bu_4NI$ was added to the phenoxide solution and heated at reflux for 5 h. After cooling to room temperature, the mixture was diluted 25 fold with EtOAc, the organics washed with saturated $NaHCO_3$ (aq) and $H_2O$ and concentrated under reduced pressure. Material was purified by flash chromatography ($SiO_2$, 10% MeOH in $CHCl_3$); yielding title compound in 71% yield from the phenol.

$^1$H NMR (CDCl$_3$) δ 7.83–7.88 (m, 3H), 7.71–7.75 (m, 2H), 7.50 (d, J=5.7 Hz, 1H), 7.38 (d, J=8.5 Hz, 2H), 7.29–7.34 (m, 2H), 7.06 (d, J=8.2 Hz, 2H), 6.79–6.88 (m, 4H), 4.34 (t, J=4.1 Hz, 2H), 4.21 (s, 2H), 4.08 (t, J=3.7, 2H), 3.94 (t, J=3.0 Hz, 2H), 3.24 (t, J=4.0 Hz, 2H), 3.12 (s, 4H), 2.03–2.24 (m, 2H), 2.02 (s, 4H); FDMS 616.3.

B. 2-[4-(3-Aminopropoxy)phenyl)-3-[4-[2-(1-pyrrolidinyl)ethoxy]benzylbenzo[b]thiophene.

To the above phthalimide (338 mg, 0.548 mmol), in EtOH (3 mL), was added $H_2NNH_2.H_2O$ (85%, 0.17 mL, 5.48 mmol) and the mixture heated at 65° C. for 1 h. After cooling to room temperature, the mixture was concentrated under reduced pressure and the resulting residue taken up in EtOAc. The organics were washed with saturated $NaHCO_3$ (aq) and $H_2O$ and reconcentrated. Material was purified by flash chromatography ($SiO_2$, 10% NeOH in $CHCl_3$ with 1% $Et_3N$ v/v added); yielding the title compound in 73% yield.

$^1$H NMR (CDCl$_3$) δ 7.82 (d, J=8.4 Hz, 1H), 7.51 (d, J=6.3 Hz, 1H), 7.41 (d, J=8.6 Hz, 2H), 7.28 (m, 2H), 7.03 (d, J=8.4 Hz, 2H), 6.91 (d, J=8.6 Hz, 2H), 6.81 (d, J=8.4 Hz, 2H), 4.19 (s, 2H), 4.10 (m, 4H), 3.02 (s, 2H), 2.90 (t, J=5.9 Hz, 2H), 2.65 (s, 4H), 2.04 (m, 2H), 1.82 (s, 4H); FDMS 487 (M+1).

PREPARATION 4

Preparation of 1-[2-[4-[[2-[4-(4-Aminobutoxy)phenyl]benzo[b]thiophen-3-yl]methyl]phenoxy]ethyl]pyrrolidine

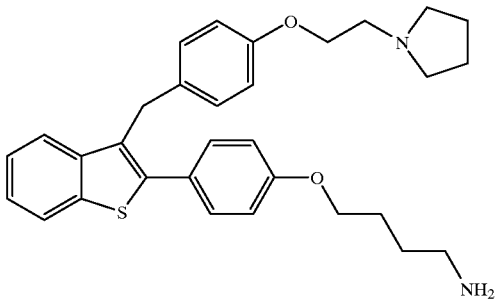

A. 1-[2-[4-[[2-[4-[4-(N-Phthalimidyl)butoxy]phenyl]benzo[b]thiophen-3-yl]methyl]phenoxy]ethyl]pyrrolidine.

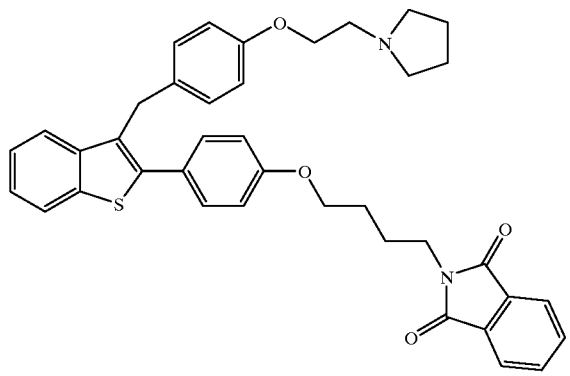

To a solution of 1-[2-[4-[[2-(4-hydroxyphenyl)benzo[b]thiophen-3-yl]methyl]phenoxy]ethyl]pyrrolidine (Preparation 2, Part D or G; 53 mg, 0.123 mmol) in THF (1 mL) was added a solution of potassium bis(trimethylsilyl)amide (0.271 mL of 0.5 M, 1.36 mmol, 1.1 eq.) in toluene at ambient temperature. After 80 min, N-(4-bromobutyl)phthalimide (75 mg, 0.265 mmol, 2.2 eq) was added and the reaction heated at ref lux for 18 h. The reaction was cooled to ambient temperature, diluted with ethyl acetate (50 mL) then washed with 10% aqueous sodium bicarbonate (20 mL). The solvent was removed under reduced pressure then the residue purified by flash chromatography (20:1 $CHCl_3$:MeOH then 5:1 $CHCl_3$:MeOH) to give the protected amine as a tan solid (54 mg, 70%) and recovered starting material (8 mg).

$^1$HNMR (300 MHz, CDCl$_3$) δ 7.83 (dd, J=8.6, 5.6 Hz, 1H), 7.69 (dd, J=5.1, 2.9 Hz, 1H), 7.48 (d, J=8.4 Hz, 1H), 7.38 (d, J=8.3 Hz, 2H), 7.28 (m, 3H), 7.03 (d, J=8.3 Hz, 2H), 6.89 (d, J=8.5 Hz, 2H), 6.80 (d, J=8.3 Hz, 2H), 4.18 (s, 2H), 4.07 (t, J=5.9 Hz, 2H), 4.00 (t, J=5.7 Hz, 2H), 3.77 (t J=6.2 Hz, 2H), 2.89 (t, J=5.9 Hz, 2H), 2.63 (bm, 4H), 1.82 (bm, 4H), 1.80 (bm, 4H); FDMS m/e=630 (M+); IR (CDCl$_3$) 1773, 1712, 1656, 1510, 1504, 1399, 1243 cm$^{-1}$; Anal. Cal'c for $C_{39}H_{34}N_2O_{10}S\ H_2O$: C, 66.65 H, 5.46 N, 3.97 found: C, 67.17 H, 5.47 N, 4.04.

B. 1-[2-[4-[[2-[4-(4-Aminobutozy)phenyl]benzo[b]thiophen-3-yl]methyl]phenoxy]ethyl]pyrrolidine.

To a solution of 1-[2-[4-[[2-[4-[4-(1-phthalimidyl)butoxy]phenyl]benzo[b]thiophen-3-yl]methyl]phenoxy]ethyl]pyrrolidine (389 mg, 0.617 mmol) in 95% ethanol (1.5 mL) and dichloromethane (1.5 mL) was added hydrazine hydrate (85% w/w, 0.228 mL, 6.17 mmol, 10 eq.). The reaction mixture was heated at reflux for 2 h. The reaction mixture was cooled to ambient temperature; then the solvent removed under reduced pressure. The residue was taken up in ethyl acetate (50 mL) and water (50 mL); then the organic layer was separated and washed with brine (20 mL). The solvent was removed under reduced pressure; then the residue purified by flash chromatography (9:1 CHCl$_3$:MeOH, 1% TEA) to give the amine as a soft tan solid (269 mg, 87%).

$^1$HNMR (300 MHz, CDCl$_3$) δ 7.87 (dd, J=8.2, 2.0 Hz, 1H), 7.55 (dd, J=8.8, 2.1 Hz, 1H), 7.45 (d, J=8.6 Hz, 2H), 7.27 (m, 2H), 7.09 (d, J=8.4 Hz, 2H), 6.96 (d, J=8.7 Hz, 2H), 6.85 (d, J=8.5 Hz, 2H), 4.24 (s, 2H), 4.13 (t, J=6.9 Hz, 2H), 4.05 (t, J=6.3 Hz, 2H), 2.96 (t, J=5.9 Hz, 2H), 2.82 (m, 2H), 2.70 (bm, 4H), 2.09 (m, 2H), 1.86 (bm, 4H), 1.67 (bm, 2H); FDMS m/e=501 (M+H); IR (CDCl$_3$) 2939, 1609, 1510, 1246, 1176 cm$^{-1}$; Anal. Cal'c for C$_{31}$H$_{36}$N$_2$O$_2$S.0.5 H$_2$O: C, 72.99 H, 7.32 N, 5.49 found: C, 72.99 H, 7.36 N, 5.18.

PREPARATION 5

Preparation of 2-(4-Aminophenyl)-3-[4-(2-(1-pyrrolidinyl)ethoxy]benzyl]benzo[b]thiophene

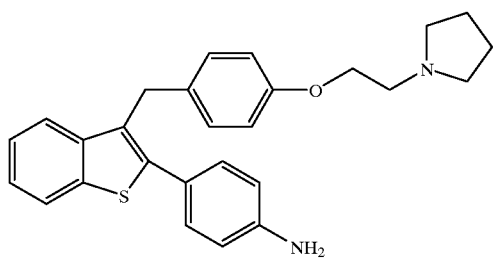

C$_2$H$_2$O$_4$

A. 2-Dimethylaminobenzo[b]thiophene-3-yl 4-Nitrophenyl Ketone.

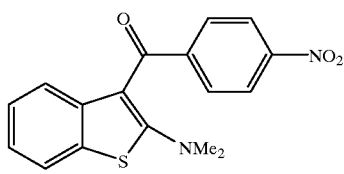

A mixture of 5.00 g (28.2 mmol) of 2-dimethylaminobenzo[b]thiophene (Vesterager et al., Tetrahedron, 1973, 29, 321–329) and 6.3 g (33.9 mmol) of 4-nitrobenzoyl chloride in 100 mL of chlorobenzene was heated at 105° C. for 6 h. The reaction was cooled and concentrated in vacuo. Purification of the residue by flash chromatography (SiO$_2$; 5% then 10% then 25% EtOAc in hexanes) afforded 7.51 g (23.0 mmol; 82%) of the title compound as burgundy flakes.

FDMS 326 (M+); Anal. calcd for C$_{17}$H$_{14}$N$_2$O$_3$S: C, 62.56; H, 4.32; N, 8.58. Found: C, 62.71; H, 4.04; N, 8.37.

B. 2-Dimethylaminobenzo[b]thiophene-3-yl 4-[2-(1-Pyrrolidinyl)ethoxy]phenyl Ketone.

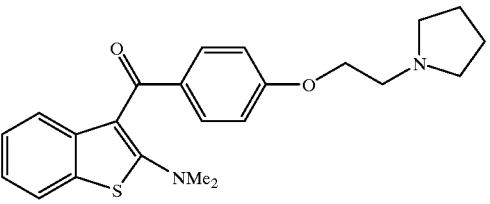

A mixture of 7.00 g (21.4 mmol) of 2-dimethylaminobenzo[b]thiophene-3-yl 4-nitrophenyl ketone (Part A) and sodium hydride (2.0 g, 50 mmol; 60% dispersion in mineral oil) in 150 mL of DMF was treated slowly with a solution of 5.30 mL (45.3 mmole) of 1-(2-hydroxyethyl)pyrrolidine in 25 mL of DMF. The reaction was stirred at ambient temperature for 4 hrs, cooled to 0° C. and quenched by the careful addition of 10 mL of H$_2$O. The solution was poured into 500 mL of H$_2$O and the mixture extracted with EtOAc (5×100 mL). The combined organic layers were washed with H$_2$O (3×100 mL), dried over K$_2$CO$_3$, filtered, and concentrated in vacuo to give 12.41 g of an oil. Purification by MPLC (0.5% then 1% then 2% MeOH in CHCl$_3$ sat'd with NH$_4$OH) afforded a quantitative yield of the title compound as an oil.

FDMS 394 (M+); Anal. calcd for C$_{23}$H$_{26}$N$_2$O$_2$S.0.3MeOH: C, 69.25; H, 6.78 N, 6.93 Found: C, 69.15; H, 6.76; N, 6.98.

C. 2-(4-Aminophenyl)benzo[b]thiophene-3-yl 4-[2-(1-Pyrrolidinyl)ethoxyiphenyl Ketone.

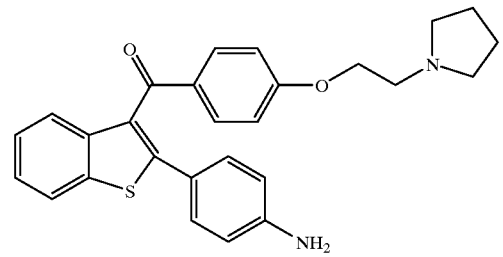

A 3-neck flask containing 580 mg of Mg ribbon was flame-dried under a stream on N$_2$. A solution of 6.7 mL (23.7 mmol) of 4-bromo-N,N-bis(trimethylsilyl)aniline in 15 mL of THF was introduced via cannula and the mixture heated 5 to 60° C. until all the Mg had been consumed. The warm mixture was added via cannula to a 0° C. solution of 8.40 g (21.3 mmol) of 2-dimethylaminobenzo[b]thiophene-3-yl 4-[2-(1-pyrrolidinyl)ethoxy]phenyl ketone (Part B) in 80 mL of THF. The reaction was stirred for 3 h and was quenched by the addition of 150 mL of sat'd aq. NH$_4$Cl. The two layers were separated and the aqueous layer was extracted with EtOAc (3×300 mL). The combined organic layers were dried over K$_2$CO$_3$, filtered and concentrated in vacuo to give 11.91 g of an oil.

The crude product was taken up in 250 mL of THF and was treated with 30 mL of a 1 M solution of tetrabutylammonium fluoride in THF. The reaction was stirred for 1 hr and was poured into 300 mL of sat'd ag NaHCO$_3$. The two layers were separated and the aqueous layer extracted with EtOAc (4×150 mL). The combined organic layers were dried over K$_2$CO$_3$, filtered and concentrated in vacuo to give an oil. Purification by MPLC (SiO$_2$; 30% then 40% then 50% THF in hexanes containing 5% triethylamine) afforded 8.31 g (18.8 mmol; 88% over two steps) of the title compound as a yellow foam.

FDMS 442 (M+); Anal. calcd for $C_{27}H_{26}N_2O_2S \cdot C_2H_2O_4 \cdot 1.2\ H_2O$: C, 62.85 H, 5.53; N, 5.05. Found: C, 62.52; H, 5.14; N, 4.77.

D. 2-(4-Aminophenyl)-3-[4-[2-(1-pyrrolidinyl)ethoxy]benzyl]benzo[b]thiophene.

By essentially following the conditions described in Preparation 2, Part D, the free base of the title compound was prepared as an oil from 2-(4-aminophenyl)benzo[b]thiophene-3-yl 4-[2-(1-pyrrolidinyl)ethoxy]phenyl ketone (Part C) in 85% yield following MPLC ($SiO_2$; 30% then 40% THF with 5% TEA in hexanes). The product was converted to the dioxalate salt using two molar equivalents of oxalic acid and a similar procedure to that of Preparation 2-H, above.

FDMS 442 (M+); Anal. calcd for $C_{27}H_{28}N_2OS \cdot 2C_2H_2O_4$: C, 61.17; H, 5.30; N, 4.60. Found: C, 61.38; H, 5.57; N, 4.43.

PREPARATION 6

Preparation of 6-Benzyloxy-3-[3-methyl-4-[(1-pyrrolidinyl)methyl]benzyl]-2-(4-hydroxyphenyl)benzo[b]thiophene

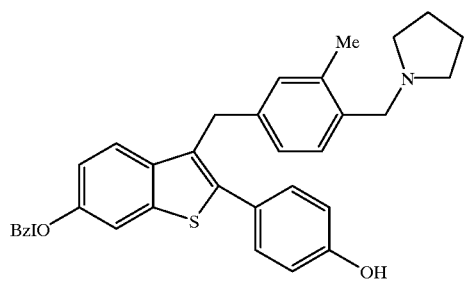

The above named phenolic intermediate useful for preparations corresponding to Preparations 2–4 may be prepared as follows.

A. α-(4-Benzyloxyphenyl)-α-hydroxy-N,N-dimethylthioacetamide.

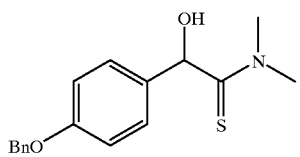

To a solution of distilled diisopropylamine (22.9 mL, 175 mmol) in 400 mL of anhydrous THF at −78° C. was added 1.6 M n-butyllithium in hexanes (100 mL, 160 mmol) over a period of 45 min. The mixture was stirred at −78° C. for 1.5 h. To the solution was cannulated over a period of 1 h a solution of 4-benzyloxybenzaldehyde (30.9 g, 146 mmol) and N,N-dimethylthioformamide (13.7 mL, 160 mmol) in 100 mL of distilled THF. The reaction mixture was stirred at −78° C. for 16 h. The reaction was then quenched with 500 mL of saturated $NH_4Cl$ solution. The mixture was extracted with EtOAc (3×1 L), and the combined organic layers were dried over $MgSO_4$ and concentrated under reduced pressure. The residue was then recrystallyzed from EtOAc/hexanes to afford 20.0 g (66.5 mmol, 46%) of an off-white solid.

mp 104–107° C.; FDMS 301 (M+); Anal. Calcd for $C_{17}H_{19}NO_2S$: C, 67.75; H, 6.35; N, 4.65. Found: C, 67.61; H, 6.37; N, 4.57.

B. 6-Benzyloxy-2-(dimethylamino)benzo[b]thiophene.

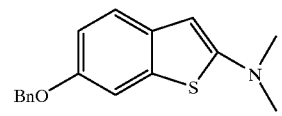

To a solution of thioacetamide (Part G) (500 mg, 1.66 mmol) in 65 mL of dry dichloroethane at room temperature was added dropwise methanesulfonic acid (0.54 ml, 8.3 mmol). The red reaction mixture was stirred for 1.5 h and then poured into 10 mL of saturated aqueous $NaHCO_3$ solution, followed by addition of 3 mL of $H_2O$, and stirred vigorously. The layers were separated and the organic layer was dried over $MgSO_4$ and concentrated under reduced pressure. The residue was then purified by flash chromatography (silica gel, 10% $Et_2O$/hexanes) to afford 327 mg (1.15 mmol, 70%) of a white solid.

mp 78–81° C.; FDMS 283 (M+); Anal. Calcd for $C_{17}H_{17}NOS$: C, 72.05; H, 6.05; N, 4.94. Found: C, 72.22; H, 6.15; N, 4.89.

C. 6-Benzyloxy-2-(dimethylamino)benzo[b]thiophen-3-yl 3-Methyl-4-(1-pyrrolidinylmethyl)phenyl Ketone.

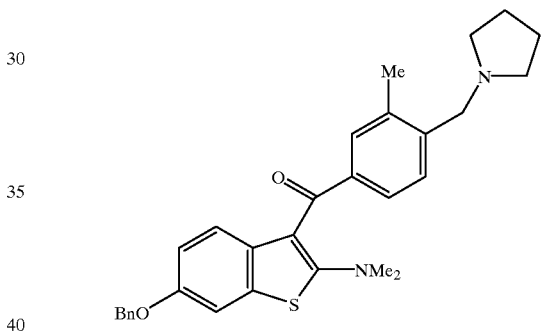

The title compound was prepared from 3-methyl-4-[(1-pyrrolidinyl)methyl]benzoic acid HCl (Preparation 1, Part C) in 80% yield as a brilliant orange solid essentially as follows:

Oxalyl chloride (2.57 mL, 29.5 mmol) was added to a stirred suspension of 3-methyl-4-[(1-pyrrolidinyl)methyl]benzoic acid hydrochloride (1.76 g, 5.90 mmol) in anhydrous $ClCH_2CH_2Cl$ (12 mL), followed by the addition of 2 drops of DMF. The suspension was stirred at room temperature under nitrogen atmosphere for 6 h, then it was concentrated to dryness under vacuum at 50° C.

To the crude benzoyl chloride obtained and suspended in anhydrous chlorobenzene (10 mL) was added 2-dimethylamino-6-benzyloxybenzo[b]thiophene (4.92 mmol) The resultant mixture was heated in an oil bath at 110° C. for 2 h. After cooling to room temperature, the mixture was diluted with EtOAc (80 mL), washed with saturated $NaHCO_3$ (25 mL), dried over $MgSO_4$, filtered, concentrated, and chromatographed on silica [gradient 0–10% $EtOH/Et_3N$ (2/1) in THF/hexanes (1/1)] to give the ketone.

FDMS 484 (M+); Anal. calcd for $C_{30}H_{32}N_2O_2S \cdot HCl$: C, 69.15; H, 6.38; N, 5.38. Found: C, 69.36; H, 6.39; N, 5.42.

D. 6-Benzyloxy-2-[(4-triisopropylsilyloxy)phenyl]benzo[b]thiophen-3-yl 3-Methyl-4-(1-pyrrolidinylmethyl)phenyl Ketone.

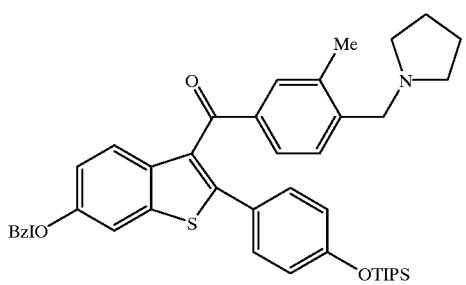

A flamed-dried flask containing 71.0 mg (2.92 mmol) of Mg ribbon was treated with a solution of 1.00 g (3.04 mmol) of 1-bromo-4-(triisopropylsilyloxy)benzene in 6 mL of THF. The mixture was treated with a small crystal of iodine and was heated to mild reflux until all the Mg had been consumed (about 2–3 h). The warm mixture was added via cannula to a 0° C. solution of 982 mg (2.03 mmol) of 6-benzyloxy-2-(dimethylmino)benzo[b]thiophen-3-yl 3-methyl-4-(1-pyrrolidinylmethyl)phenyl ketone (Part C, above) in 20 mL of THF and the solution stirred for 2 h. The cold reaction was quenched by the addition of 50 mL of sat'd aq $NH_4Cl$. The two layers were separated and the aqueous layer was extracted with EtOAc (3×100 mL). The combined organic layers were dried over $K_2CO_3$, filtered and concentrated in vacuo to give an oil. Purification by flash chromatography ($SiO_2$; 2% THF and 5% TEA in hexanes) afforded 1.17 g (1.77 mmol; 87%) of the title compound as a bright yellow oil.

FDMS 690 (M+); Anal. calcd for $C_{43}H_{51}NO_3SSi$: C, 74.85; H, 7.45; N, 2.03. Found: C, 75.07; H, 7.43; N, 1.97.

E. 6-Benzyloxy-2-(4-hydroxyphenyl)benzo[b]thiophen-3-yl 3-Methyl-4-(1-pyrrolidinylmethyl)phenyl Ketone.

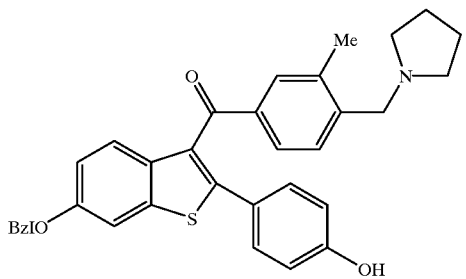

A solution of 8.74 g (13.2 mmol) of 6-benzyloxy-2-[(4-triisopropylsilyloxy)phenyl]benzo[b]thiophen-3-yl 3-methyl-4-(1-pyrrolidinylmethyl)phenyl ketone (Part D) in 200 mL of THF was treated with 14.5 mL of a 1M solution of tetrabutylammonium fluoride in THF (14.5 mmol). The burgundy colored reaction was stirred for 15 min and was poured into 250 mL of sat'd aq $NaHCO_3$. The two layers were separated and the aqueous layer was extracted with EtOAc (4×100 mL). The combined organic layers were dried over $K_2CO_3$, filtered and concentrated in vacuo to give 8.74 g of a yellow oil. A 200 mg sample was purified by radial chromatography ($SiO_2$; 1% MeOH in $CHCl_3$ sat'd with $NH_4OH$) to afford 157 mg (95% based on 8.74 g of crude material) of the title compound as a yellow solid.

FDMS 533 (M+); Anal. Calcd for $C_{34}H_{31}NO_3S$.0.5 MeOH: C, 75.38; H, 6.05; N, 2.55. Found: C, 75.25; H, 6.15; N, 2.82.

F. 6-Benzyloxy-3-[3-methyl-4-[(1-pyrrolidinyl)methyl]benzyl]-2-(4-hydroxyphenyl)benzo[b]thiophene.

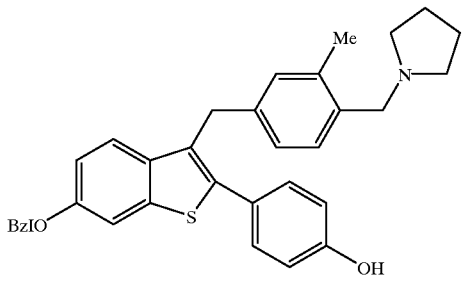

By essentially following the conditions described in Preparation 2, Part D, the title compound was prepared as a foam in 74% yield from 6-benzyloxy-2-(4-hydroxyphenyl)benzo[b]thiophen-3-yl 3-methyl-4-(1-pyrrolidinylmethyl)phenyl ketone (Part E).

FDMS 520 (M+1).

PREPARATION 7

Preparation of 2-(4-Aminophenyl)-6-benzyloxy-3-[3-methoxy-4-[(1-pyrrolidinyl)methyl]benzyl]benzo[b]thiophene

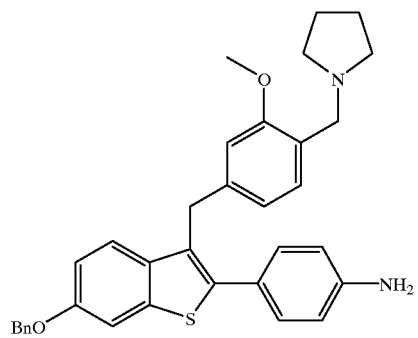

A. Methyl 3-Methoxy-4-[(1-pyrrolidinyl)methyl]benzoate.

Following the procedures of Preparation 1, Parts A and B, above, the substituted pyrrolidine was obtained from methyl 3-methoxy-4-methylbenzoate as an oil in 65% yield.

IR ($CHCl_3$) 2954, 1716 cm$^{-1}$; $^1H$ NMR ($CDCl_3$) δ 1.95 (br s, 4H), 2.89 (br s, 4H), 3.91 (s, 3H), 3.92 (s, 3H), 3.98 (br t, J=6.8 Hz, 2H), 7.56 (s, 1H), 7.61–7.67 (m, 2H); FDMS m/e 249 (M+).

B. 3-Methoxy-4-[(1-pyrrolidinyl)methyl]benzoic Acid Hydrochloride.

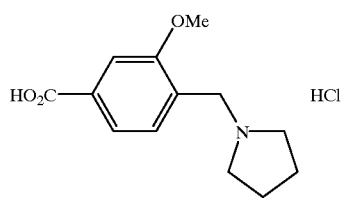

Following the procedure of Preparation 1, Part C, above, the acid was obtained from the above ester as a yellowish solid in 65% crude yield.

$^1H$ NMR (DMSO-$d_6$) δ 1.89–1.94 (br s, 4H), 3.01–3.05 (br s, 2H), 3.26–3.34 (br s, 2H), 3.88 (s, 3H), 4.32 (s, 2H), 7.53 (s, 1H), 7.54 (d, J=7.7 Hz, 1H), 7.70 (d, J=7.7 Hz, 1H); FDMS m/e 235 (M+).

C. 6-Benzyloxy-2-(dimethylamino)benzo[b]thiophen-3-yl 3-Methoxy-4-[(1-pyrrolidinyl)methyl]phenyl Ketone.

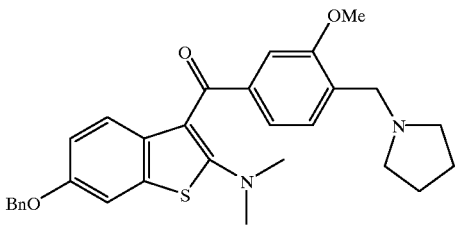

Following the procedure of Preparation 6, Part C, the ketone was obtained in 81% yield from the above acid and 6-benzyloxy-2-dimethylaminobenzo[b]thiophene as a foam.

IR (CHCl$_3$) 2970, 1621, 1600 cm$^{-1}$; $^1$H NMR (CDCl$_3$) δ 1.85 (br s, 4H), 2.70 (br s, 4H), 2.89 (s, 6H), 3.80 (s, 2H), 3.88 (s, 3H), 5.08 (s, 2H), 6.89 (dd, J=8.9 and 2.5 Hz, 1H), 7.20 (d, J=2.3 Hz, 1H), 7.33–7.47 (m, 9H); FDMS m/e 500 (M$^+$).

D. 6-Benzyloxy-2-[4-[bis(trimethylsilyl)amino]phenyl]benzo[b]thiophen-3-yl 3-Methoxy-4-[(1-pyrrolidinyl)methyl]phenyl Ketone.

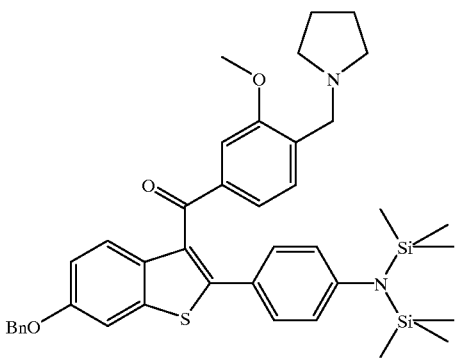

Magnesium turnings (0.25 g) were placed in a two-neck 100 mL round-bottom flask fitted with a reflux condenser and a magnetic stir bar The whole apparatus was flame-dried and allowed to cool to ambient temperature. Dry THF (17 mL) and a small crystal of iodine were then introduced followed by slow addition of 4-bromo-N,N-bis(trimethylylsilyl)aniline (3.36 g) while stirring at ambient temperature. The reaction mixture was warmed to a gentle reflux for 1.5 h or until magnesium turnings were completely consumed to give a 0.5 M solution of the Grignard reagent. This freshly prepared Grignard solution (15 mL) was added slowly to a stirring solution of 6-benzyloxy-2-(dimethylamino)benzo[b]thiophen-3-yl 3-methoxy-4-[(1-pyrrolidinyl)methyl]phenyl ketone (2.48 g, 5.0 mmol) in THF (15.0 mL) at 0° C. under argon. The mixture was stirred at 0° C. for 3 h before quenched with saturated aqueous NH$_4$Cl solution (50 mL) and extracted with CH$_2$Cl$_2$ (50 mL×3). The combined organic layers were dried with sodium sulfate and concentrated under reduced pressure. Chromatography with EtOAc-hexane (0–100% gradient elution) afforded the title compound (0.73 g).

FDMS m/e: found 693(M$^+$); $^1$H NMR(CDCl$_3$): δ 7.74(d, 1H), 7.55–7.35(m,7H), 7.28(d,2H), 7.22(d, 1H), 7.20(d,1H), 7.10(d,1H), 6.68(d,2H), 5.17(s,2H), 3.76(s, 3H), 3.55(s,2H), 2.51(m, 4H), 1.78(m, 4H), 0.00(s,18H).

E. 6-Benzyloxy-3-[3-methoxy-4-[(1-pyrrolidinyl)methyl]benzyl]-2-(4-aminophenyl)benzo[b]thiophene.

6-Benzyloxy-2-[4-[bis(trimethylsilyl)amino]phenyl]benzo[b]thiophen-3-yl 3-methoxy-4-[(1-pyrrolidinyl)methyl]phenyl ketone (0.73 g) was dissolved in THF (10 mL), cooled to 0° C. in an ice bath before treated with lithium aluminum hydride (110 mg) at 0° C. for 1 h, then quenched with water(1 mL) and sodium hydroxide (1.0 M, 1 mL). Stirring continued for 30 min. The reaction mixture was diluted with brine(30 mL) and extracted with dichloromethane (20 mL×3). The combined organic layers were dried with sodium sulfate and concentrated in vacuo to give the crude alcohol. This material was dissolved in dichloromethane (15 mL), treated with triethylsilane (1.5 mL) and trifluroacetic acid (1.5 mL) sequentially, allowed to stir at ambient temperature for 1.5 h, and concentrated under reduced pressure. The residue was extracted with dichloromethane (20 mL×3) from saturated aqueous sodium bicarbonate (30 mL). The combined organic layers were dried with sodium sulfate and concentrated. Chromatography with Et$_3$N:MeOH:EtOAc (5:5:90) afforded the title compound as a yellow foam (0.53 g).

FDMS m/e: found 535(M+H$^+$); $^1$H NMR(CDCl$_3$): δ 7.60–7.45(m,7H), 7.30(d,2H), 6.98(d, 1H), 6.70(m,4H), 5.13(s,2H), 4.21(s, 2H), 3.78(s,2H), 3.70(s,3H), 3.62(s,2H), 2.56(m, 4H), 1.78(m, 4H).

PREPARATION 8

Preparation of 2-(4-Aminophenyl)-6-hydroxy-3-[3-methoxy-4-(1-pyrrolidinyl)-benzyl]benzo[b]thiophene

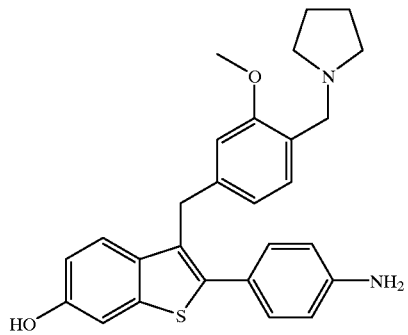

2-(4-Aminophenyl)-6-benzyloxy 3-[3-methoxy-4-[(1-pyrrolidinyl)methyl]benzyl]benzo[b]thiophene (103 mg) in THF (4.0 mL) was treated with a solution of ammonium formate (25% in H$_2$O, 2.0 mL) and 10% palladium on carbon (100 mg) sequentially at ambient temperature. The resulting mixture was stirred at ambient temperature under argon for 21 h before filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et$_3$N:MeOH:EtOAc (5:10:85) afforded the product (80 mg).

$^1$H NMR(CDCl$_3$): δ 7.23(d,2H), 7.18(d,1H), 7.15(d, 1H), 7.13(s, 1H), 6.67(d,3H), 6.62(s,1H), 6.42(d,1H), 4.17(s, 2H), 3.74(s, 2H), 3.52(s,3H), 2.74(m, 4H), 1.83(m, 4H).

PREPARATION 9

Preparation of 2-[4-(Cyanomethoxy)phenyl]-3-[4-[2-(1-pyrrolidinyl)ethoxy]benzyl]benzo[b]thiophene

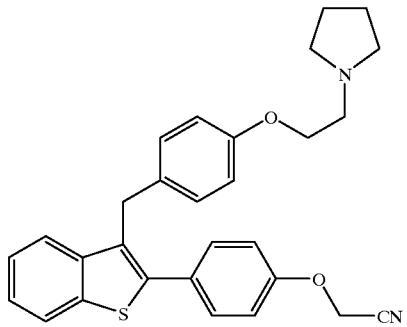

A suspension of 2-(4-hydroxyphenyl)-3-[4-[2-(1-pyrrolidinyl)ethoxy]benzyl]benzo[b]thiophene (102 mg) and cesium carbonate (386 mg) in DMF (3.0 mL) was treated with bromoacetonitrile (20 uL) while stirring at ambient temperature.

Stirring was continued for 2 h and the reaction mixture was diluted with brine (30 mL) and extracted with EtOAc (20 mL×3). The combined organic layers were dried with sodium sulfate and concentrated under reduced pressure. Chromatography with Et$_3$N-EtOAc (0–5%) afforded the product (98 mg).

FDMS m/e: found 469(M+H$^+$); $^1$H NMR(CDCl$_3$): δ 7.88(d,1H), 7.59(d,1H), 7.57(d, 2H), 7.34(m, 2H), 7.09(d, 2H), 7.03(d,2H), 6.85(d,2H), 4.82(s, 2H), 4.24(s, 2H), 4.14 (t, 2H), 3.00(t,2H), 2.73 (m, 4H), 1.86(m, 4H).

PREPARATION 10

Preparation of 2-[4-(2-Aminoethyl)phenyl]-6-benzyloxy-3-[3-methoxy-4-[(1-pyrrolidinyl)methyl]benzyl]benzo[b]thiophene

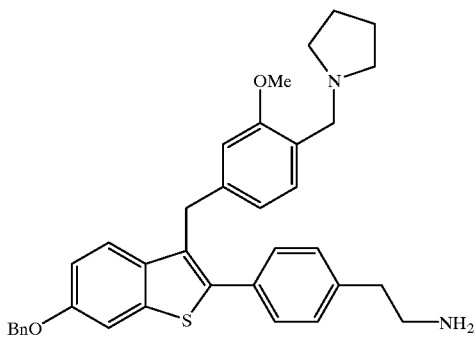

A. 2-[4-(2-Aminoethyl)phenyl]-6-benzyloxybenzo[b]thiophen-3-yl 3-Methoxy-4-[(1-pyrrolidinyl)methyl]phenyl Ketone.

4-(2-Aminoethyl)bromobenzene (1.7 g; 8.4 mmol) and 2.3 mL (2 eq) of Et$_3$N were comrbined with 3 mL of anhydrous DMF in a flame-dried, argon-filled flask. 1,2-Bis (chlorodimethylsilyl)ethane was added in 3.0 mL of DMF. The mixture was stirred at room temperature for 2 h. The mixture was filtered through a sintered glass funnel, and concentrated under reduced pressure. The colorless oil subsequently crystallized.

The protected bromobenzene derivative was converted to the corresponding Grignard reagent. Magnesium (33 mg; 1.35 mmol) was placed in a flask which was subsequently flame-dried and filled with argon. Anhydrous THF (3 mL) and the protected aminoarylbromide were added with a small crystal of I$_2$. The mixture was heated under reflux for 3 h. The resulting reagent was used without purification.

The aminobenzothiophene described above in Preparation 7, Part C, (4.10 g; 8.2 mmol) was dissolved in anhydrous THF in a flame-dried, argon-filled flask, and cooled in an ice-water bath. The Grignard reagent prepared above (1.5 eq) was added dropwise. The mixture was stirred in the cold for 1 h, then saturated NH$_4$Cl was added, and extraction was carried out with CH$_2$Cl$_2$. The combined organics were dried by passage through Na$_2$SO$_4$. The product (4.2 g of yellow oil; 89% yield) was purified by flash chromatography on silica gel, eluting with a gradient of EtOAc(100–85%)/Et$_3$N (0–5%)/NH$_4$OH(0–5%).

$^1$H NMR (CDCl$_3$) δ 7.63 (d, J=8.9 Hz, 1H), 7.5–7.2 (m, 11H), 7.05 (m, 3H), 5.16 (s, 2H), 3.79 (s, 3H), 3.61 (s, 2H), 2.89 (t, J=6.6 Hz, 2H), 2.67 (t, J=6.7 Hz, 2H), 2.50 (br s, 4H), 1.77 (br s, 4H), 1.40 (br s, 2H). FDMS 577.1 (M+1).

B. 2-[4-(2-Aminoethyl)phenyl]-6-benzyloxy-3-[3-methoxy-4-[(1-pyrrolidinyl)methyl]benzyl]benzo[b]thiophene.

Using a procedure similar to that described in Preparation 2, Part G, (except using EtOAc instead of CH$_2$Cl$_2$ in the final work up), the above ketone (Part B) was reduced to the title compound compound in 59% yield. Purification was carried out by flash chromatography on silica gel, eluting with a gradient of EtOAc(100–85%)/MeOH(0–10%)/NH$_4$OH (0–5%).

$^1$H NMR (CDCl$_3$) δ 7.47–7.33 (m, 9H), 7.23 (m, 3H), 6.98 (d, J=8.7 Hz, 1H), 6.69 (d, J=7.6 Hz, 1H), 6.65 (s, 1H), 5.13 (s, 2H), 4.23 (s, 2H), 3.69 (s, 3H), 3.63 (s, 2H), 2.98 (t, J=6.8 Hz, 2H), 2.77 (t, J=6.8 Hz, 2H), 2.57 (br s, 4H), 1.79 (br s, 4H). FDMS 563.1 (M+1).

EXAMPLE 1

Preparation of (S)-2-[4-[(2-Amino-3-benzyloxy-1-oxopropyl)amino]phenyl]-6-hydroxy-3-[3-methoxy-4-(1-pyrrolidinylmethyl)benzyl]benzo[b]thiophene

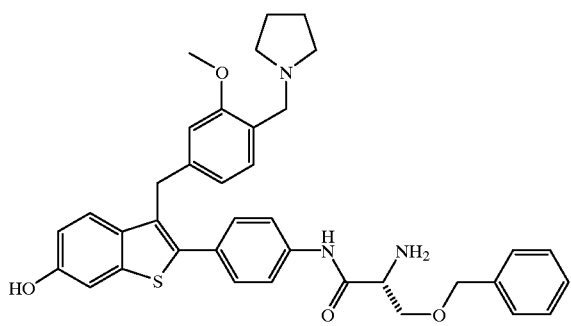

2-(4-Aminophenyl)-6-benzyloxy-3-[3-methoxy-4-(1-pyrrolidinylmethyl)benzyl]benzo[b]thiophene (Preparation 7; 273 mg) and N-benzyloxycarbonyl-O-benzyl-(L)-serine (184 mg) were dissolved in DMF (5.0 mL), treated with DCC (130 mg) and HOAt (88 mg) sequentially, and allowed to stir at ambient temperature under argon for 22 h. The reaction mixture was diluted with brine (30 mL), extracted with ethyl acetate (20 mL×3). The combined organic layers were dried with sodium sulfate and concentrated. Chromatography with Et$_3$N:EtOAc (0–3%) afforded the direct coupling product. This product was dissolved in THF (5.0 mL), treated with a solution of ammonium formate (25% in H$_2$O, 2.0 mL) and 10% palladium on carbon (100 mg) sequentially at ambient temperature. The resulting mixture was stirred at ambient temperature under argon for 45 h before it was filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et$_3$N:MeOH:EtOAc (5:10:85) followed by NH$_4$OH:MeOH:EtOAc (5:10:85) afforded the title compound (124 mg) along with a minor amount of the completely debenzylated product (20 mg) described below in Example 2.

FDMS m/e: found 622(M+H$^+$); $^1$H NMR(CDCl$_3$): δ 9.74(s,1H), 7.70(d,2H), 7.51(d, 2H), 7.43(m, 5H), 7.23 (apparent t,2H), 7.19(s, 1H), 6.75(d,1H), 6.71(s, 1H), 6.47 (d, 1H), 5.41(s,2H), 4.63(s, 2H), 4.31(s, 2H), 3.93 (d,2H), 3.81(bs,3H), 3.60(s,3H), 2.80(m,4H), 1.95(m, 4H).

EXAMPLE 2

Preparation of (S)-2-[4-[(2-Amino-3-hydroxy-1-oxopropyl)amino]phenyl]-6-hydroxy-3-[3-methoxy-4-(1-pyrrolidinylmethyl)benzyl]benzo[b]thiophene

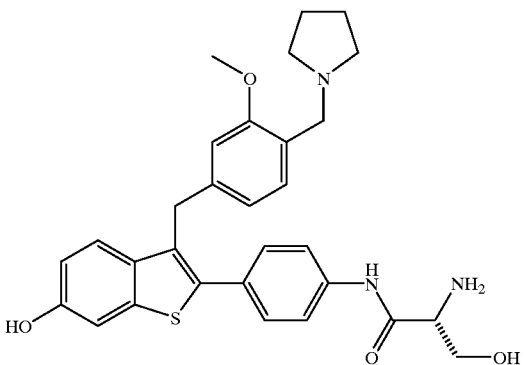

The minor product isolated in Example 1, above, was characterized as follows. (See also Example 16, below.)

$^1$H NMR(CD$_3$OD): δ 7.64(d,2H), 7.41(d, 2H), 7.37(d, 1H), 7.20(s,2H), 7.12(d, 1H), 6.79(d,1H), 6.73(s, 1H), 6.67 (d, 1H), 4.19(s, 2H), 3.76(d, 2H), 3.72(s,2H), 3.67(s,3H), 3.52(t,1H), 2.67(m,4H), 1.80(m, 4H).

EXAMPLE 3

Preparation of (S)-2-[4-[(2-Amino-3-carboxy-1-oxopropyl)amino]phenyl]-6-hydroxy-3-[3-methoxy-4-(1-pyrrolidinylmethyl)benzyl]benzo[b]thiophene

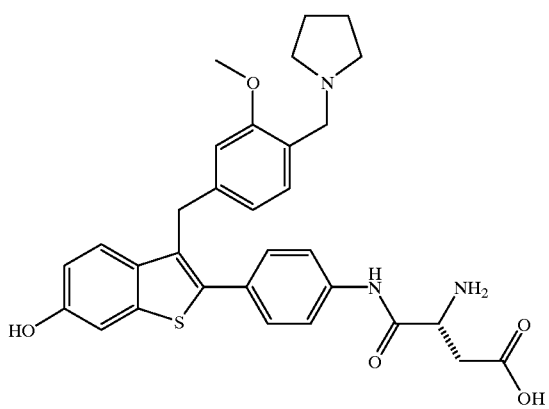

2-(4-Aminophenyl)-6-benzyloxy-3-[3-methoxy-4-(1-pyrrolidinylmethyl)benzyl]benzo[b]thiophene (267 mg) and N-t-BOC-L-aspartic acid β-t-butyl ester (260 mg) were dissolved in DMF (5.0 mL), treated with DCC (126 mg) and HOAt (84 mg) sequentially, and allowed to stir at ambient temperature under argon for 22 h. The reaction mixture was diluted with brine (30 mL), extracted with ethyl acetate (20 mL×3). The combined organic layers were dried with sodium sulfate and concentrated. Chromatography with Et₃N:EtOAc (0–5%) afforded the direct coupling product. This product was dissolved in THF (5.0 mL), treated with a solution of ammonium formate (25% in H₂O, 2.0 mL) and 10% palladium on carbon (100 mg) sequentially at ambient temperature. The resulting mixture was stirred at ambient temperature under argon for 20 h before it was filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et₃N:MeOH:EtOAc (5:0–5:95–90) afforded the debenzylation product (240 mg). This product was dissolved in EtOAc (3 mL), cooled to 0° C. under argon, treated with a solution of HCl in EtOAc (3 M, 2 mL) and allowed to stir at 0° C. for 3 h. The reaction mixture was then concentrated under reduced pressure to remove the solvent and excess HCl. The reddish residue was dissolved in THF:MeOH:H₂O (3:1:1, 1 mL), treated with LiOH (20 mg) and allowed to stir at ambient temperature for 2.5 h. The reaction mixture was concentrated and the brown residue was triturated with MeOH and the light yellow solution was separated from the dark brown precipitate by centrifugation. Evaporation of the light yellow solution afforded a light yellow solid as the title compound (45 mg).

FDMS m/e: found 560(M+H⁺); ¹H NMR(CD₃OD): δ 7.64(d,2H), 7.46(d, 2H), 7.32(d, 1H), 7.22 (d,1H), 7.07(s, 1H), 6.83(s,1H), 6.77(apparent t, 2H), 4.23 (bs,2H), 3.78(s, 3H), 3.72(s,2H), 3.44(s,2H), 2.64(m,4H), 1.83(m, 4H).

EXAMPLE 4

Preparation of (S)-2-[4-[3-[(2-Amino-3-phenyl-1-oxopropyl)amino]propoxy]phenyl]-3-[4-[2-(1-pyrrolidinyl)ethoxy]benzylbenzo[b]thiophene Bis (trifluoroacetate)

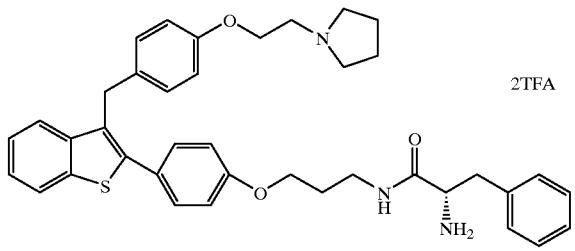

A. (S)-2-[4-[3-[(2-Boc-amino-3-phenyl-1-oxopropyl)amino]propoxy]phenyl]-3-[4-[2-(1-pyrrolidinyl)ethoxy]benzylbenzo[b]thiophene.

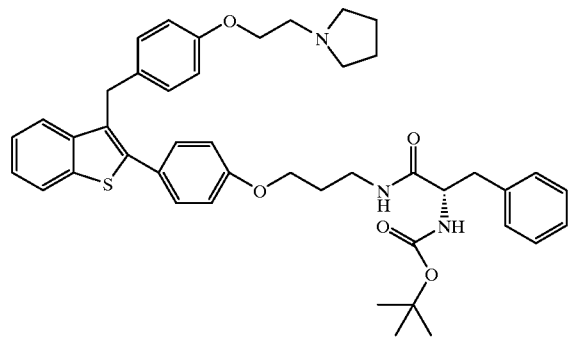

To the amine (Preparation 3; 50 mg, 0.103 mg) was added N-Boc-L-phenylalanine (27 mg, 0.103 mmol), 1-(3-dimethylaminopropyl)-3-ethylcarbodiimide hydrochloride (39 mg, 0.206 mmol), a catalytic amount of 4-dimethylaminopyridine, and CH₂Cl₂ (0.5 mL). The mixture was stirred at room temperature for 45 minutes and then diluted 50 fold with EtOAc. The organics were washed with saturated NaHCO₃ (aq), H₂O, brine, and concentrated under reduced pressure. The material was purified by flash chromatography (SiO₂, 10% MeOH in CHCl₃); yielding 66 mg (87%) of the title compound.

¹H NMR (CDCl₃) δ 7.84 (d, J=6.8 Hz, 1H), 7.51 (d, J=7.8 Hz, 1H), 7.41 (d, J=8.6 Hz, 2H), 7.18–7.34 (m, 7H), 7.06 (d, J=8.5 Hz, 2H), 6.86 (d, J=8.6 Hz, 2H), 6.82 (d, J=8.6 Hz, 2H), 4.32 (d, J=7.0 Hz, 1H), 4.21 (s, 2H), 4.15 (t, J=5.7 Hz, 2H), 3.90 (t, J=4.9 Hz, 2H), 3.39 (t, J=3.7 Hz, 2H), 3.06 (d, J=5.0 Hz, 2H), 2.99 (t, J=5.8 Hz, 2H), 2.77 (s, 4H), 1.88 (s, 6H), 1.39 (s, 9H); FDMS 734.2 (M+1).

B. (S)-2-[4-[3-[(2-Amino-3-phenyl-1-oxopropyl)amino]propoxy]phenyl]-3-[4-[2-(1-pyrrolidinyl)ethoxy[benzylbenzo[b]thiophene Bis(trifluoroacetate).

To the carbamate (Example 4, Part A; 56 mg, 0.076 mmol) was added TFA (2 mL) and the solution allowed to stand for 1 h at room temperature. After concentrating under reduced pressure, the resulting residue was triturated with Et₂O and the off white solid collected and dried under vacuum; yielding 62 mg (94%) of the title compound.

¹H NMR (CD₃OD) δ 7.82 (d, J=7.0 Hz, 1H), 7.47 (d, J=8.6 Hz, 1H), 7.40 (d, J=8.6 Hz, 2H), 7.21–7.32 (m, 7H), 7.05 (d, J=8.6 Hz, 2H), 6.90 (d, J=8.8 Hz, 2H), 6.87 (d, J=8.6 Hz, 2H), 4.24 (t, J=4.6 Hz, 2H), 4.14 (s, 2H), 4.01 (t, J=7.6 Hz, 2H), 3.82 (t, J=5.8 Hz, 2H), 3.70 (m, 2H), 3.66 (t, J=3.5 Hz, 2H), 3.40–3.58 (m, 2H), 3.08–3.30 (m, 4H), 2.07 (bd, 4H), 1.82–1.99 (m, 2H); FAB MS 634.3 (M+1).

EXAMPLE 5

Preparation of (S)-2-[4-[3-[(2-Amino-1-oxopropyl)amino[propoxy]phenyl]-3-[4-[2-(1-pyrrolidinyl)ethoxy]benzylbenzo[b]thiophene Bis (trifluoroacetate)

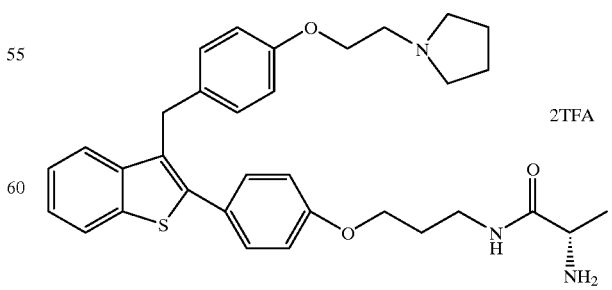

A. (S)-2-[4-[3-[(2-Boc-amino-1-oxopropyl)amino]propoxy]phenyl]-3-[4-[2-(1-pyrrolidinyl)ethoxy]benzylbenzo[b]thiophene.

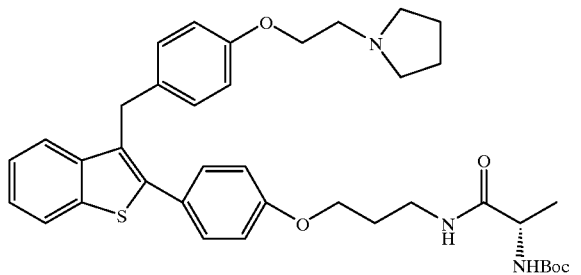

The title compound was formed in 96% yield from the amine (Preparation 3) and N-Boc-L-alanine by essentially following the procedure outlined in Example 4, Part A.

¹H NMR (CDCl₃) δ 7.86 (d, J=8.7 Hz, 1H), 7.54 (d, J=8.8 Hz, 1H), 7.45 (d, J=8.5 Hz, 2H), 7.28–7.37 (m, 2H), 7.06 (d, J=8.5 Hz, 2H), 6.96 (d, J=8.6 Hz, 2H), 6.84 (d, J=8.5 Hz, 2H), 4.24 (s, 2H), 4.19 (t, J=5.6 Hz, 3H), 4.09 (t, J=5.8 Hz, 2H), 3.51 (m, 2H), 3.04 (t, J=5.6 Hz, 2H), 2.83 (s, 4H), 2.05 (m, 2H), 1.91 (s, 4H), 1.46 (s, 9H), 1.39 (d, J=7.0 Hz, 3H); FDMS 658.4 (M+1).

B. (S)-2-[4-[3-[(2-Amino-1-oxopropyl)amino]propoxy]phenyl]-3-[4-[2-(1-pyrrolidinyl)ethoxy]benzylbenzo[b]thiophene Bis(trifluoroacetate).

The title compound was formed in 91% yield from the amide (Example 5, Part A) by essentially following the procedure outlined in Example 4, Part B.

¹H NMR (CD₃OD) δ 7.86 (d, J=8.2 Hz, 1H), 7.51 (d, J=7.2 Hz, 1H), 7.46 (d, J=8.6 Hz, 2H), 7.29 (m, 2H), 7.09 (d, J=8.5 Hz, 2H), 7.02 (d, J=8.7 Hz, 2H), 6.92 (d, J=8.5 Hz, 2H), 4.29 (t, J=5.1 Hz, 2H), 4.25 (s, 2H), 4.10 (t, J=6.0 Hz, 2H), 3.91 (m, 1H), 3.72 (bs, 2H), 3.64 (t, J=4.8 Hz, 2H), 3.50 (t, J=6.6 Hz, 2H), 3.23 (bs, 2H), 2.03–2.20 (m, 6H), 1.51 (d, J=7.1 Hz, 3H); FAB MS 558.2 (M+1).

EXAMPLE 6

Preparation of (S)-2-[4-[3-[[2-Amino-3-(4-hydroxyphenyl)-1-oxopropyl]amino]propoxy]phenyl]-3-[4-[2-(1-pyrrolidinyl)ethoxy]benzylbenzo[b]thiophene Dihydrochloride

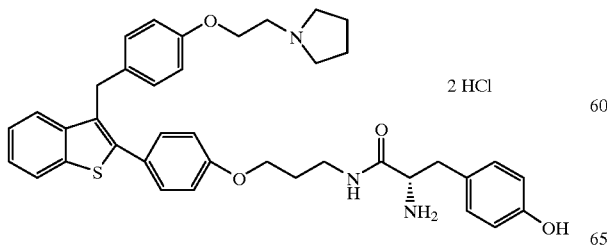

A. (S)-2-[4-[3-[[2-Boc-amino-3-(4-hydroxyphenyl)-1-oxopropyl]amino]propoxy]phenyl]-3-[4-[2-(1-pyrrolidinyl)ethoxy]benzylbenzo[b]thiophene.

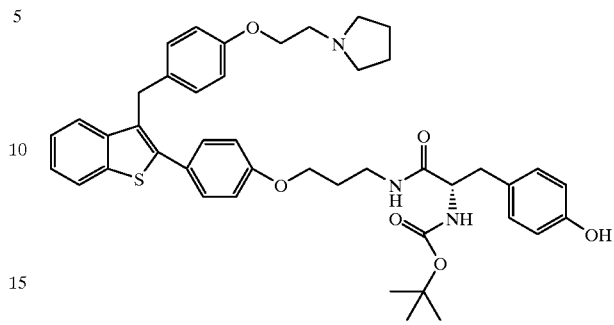

The title compound was formed in 56% yield from the amine (Preparation 3) and N-Boc-L-tyrosine by essentially following the procedure outlined in Example 4, Part A.

FDMS 750.7 (M+1).

B. (S)-2-[4-[3-[[2-Amino-3-(4-hydroxyphenyl)-1-oxopropyl]amino]propoxy]phenyl]-3-[4-[2-(1-pyrrolidinyl)ethoxy]benzylbenzo[b]thiophene Dihydrochloride.

To the Boc-tyrosine compound (Example 6, Part A; 41 mg, 0.055 mmol) was added TFA (2 mL) and the solution allowed to stand for 1 h. After concentrating under reduced pressure the resulting residue was purified by semi-preparative HPLC, using a [VYDAC] C18 column (25×250 mm), and following a gradient elution 98:2 (H₂O with 0.1% HCl added/CH₃CN) to 50:50; yielding 12 mg (30%) of the desired product.

¹H NMR (CD₃OD) δ 8.33 (m, 1H), 7.82 (d, J=7.1 Hz, 1H), 7.49 (d, J=7.4 Hz, 1H), 7.42 (d, J=8.6 Hz, 2H), 7.31–7.24 (m, 2H), 7.07 (m, 4H), 6.96–6.88 (m, 6H), 6.75 (d, J=8.4 Hz, 2H), 4.27 (t, J=4.7 Hz, 2H), 4.20 (s, 2H), 3.92 (t, J=7.1 Hz, 2H), 3.59–3.80 (m, 4H), 3.45 (m, 1H), 3.25 (m, 2H), 2.99 (t, J=6.8 Hz, 2H), 1.87–2.16 (m, 6H); FDMS 650.1 (M+1).

EXAMPLE 7

Preparation of (S)-2-[4-[3-[(2-Amino-3-carbamoyl-1-oxopropyl)amino]propoxy]phenyl]-3-[4-[2-(1-pyrrolidinyl)ethoxy]benzylbenzo[b]thiophene Dihydrochloride

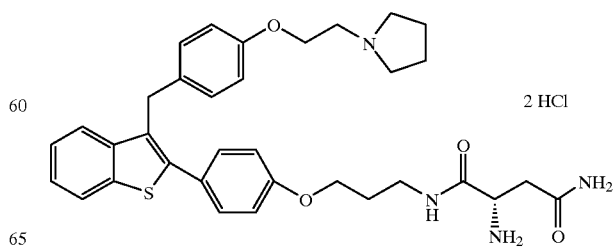

A. (S)-2-[4-[3-[(2-Boc-amino-3-carbamoyl-1-oxopropyl)amino]propoxy]phenyl]-3-[4-[2-(1-pyrrolidinyl)ethoxy]benzylbenzo[b]thiophene.

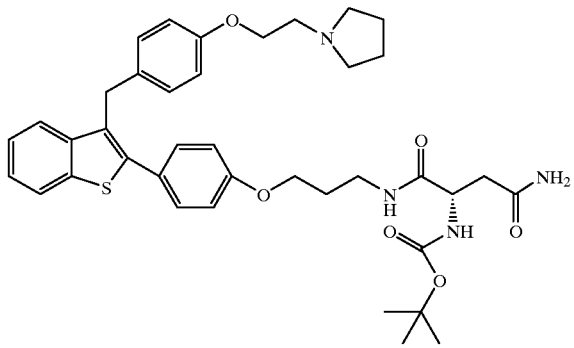

The title compound was formed in 84% yield from the amine (Preparation 3) and N-Boc-L-asparagine by essentially following the procedure outlined in Example 4, Part A.

$^1$H NMR (CDCl$_3$) δ 7.87 (d, J=8.7 Hz, 1H), 7.54 (d, J=8.9 Hz, 1H), 7.43 (d, J=8.6 Hz, 2H), 7.32 (m, 2H), 7.08 (d, J=8.5 Hz, 2H), 6.97 (d, J=8.6 Hz, 2H), 6.83 (d, J=8.5 Hz, 2H), 4.50 (s, 1H), 4.28 (t, J=5.1 Hz, 2H), 4.23 (s, 2H), 4.07 (t, J=5.9 Hz, 2H), 3.50 (t, J=5.4 Hz, 2H), 3.17 (t, J=4.8 Hz, 2H), 3.01 (s, 4H), 2.60 (dd, J=8.6 Hz, 17.2 Hz, 2H), 2.03 (m, 6H) 1.46 (s, 9H); FDMS 701.8 (M+1).

B. (S)-2-[4-[3-[(2-Amino-3-carbamoyl-1-oxopropyl)amino]propoxy]phenyl]-3-[4-[2-(1-pyrrolidinyl)ethoxy]benzylbenzo[b]thiophene Dihydrochloride.

The title compound was formed in 46% yield from the Boc-asparagine compound (Example 7, Part A) by essentially following the procedure outlined in Example 6, Part B.

$^1$H NMR (CD$_3$OD) δ 7.82 (d, J=7.2 Hz, 1H), 7.49 (d, J=6.7 Hz, 1H), 7.44 (d, J=9.9 Hz, 2H), 7.27 (m, 2H), 7.05 (d, J=8.5 Hz, 2H), 6.99 (d, J=8.6 Hz, 2H), 6.89 (d, J=8.6 Hz, 2H), 4.27 (t, J=4.7 Hz, 2H), 4.21 (s, 2H), 4.16 (m, 1H), 4.06 (t, J=6.0 Hz, 2H), 3.68 (m, 2H), 3.62 (t, J=4.6 Hz, 2H), 3.44 (m, 2H), 3.20 (m, 2H), 2.85 (m, 2H), 1.99–2.16 (m, 6H); FAB MS 601.3. (M+1).

EXAMPLE 8

Preparation of (S)-2-[4-[2-[(2-Amino-1-oxopropyl)amino]ethoxy]phenyl]-3-[4-[2-(1-pyrrolidinyl)ethoxy]benzylbenzo[b]thiophene Bis(trifluoroacetate)

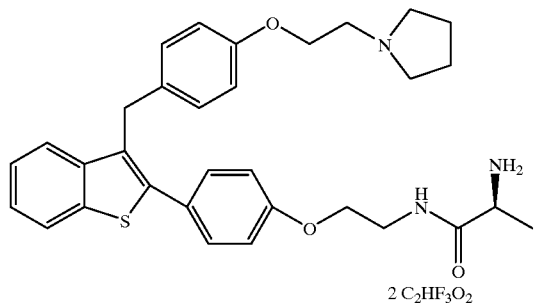

A. (S)-2-[4-[2-[(2-Boc-amino-1-oxopropyl)amino]ethoxy]phenyl]-3-[4-[2-(1-pyrrolidinyl)ethoxy]benzylbenzo[b]thiophene.

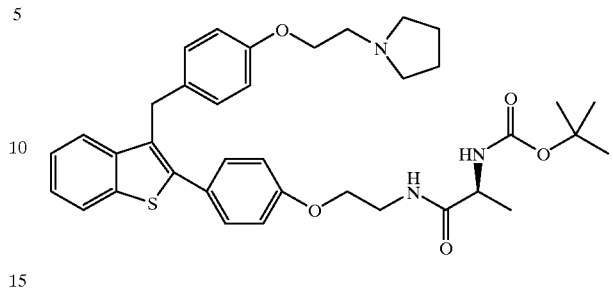

To a mixture of LAH (8 mg, 0.199 mmol), in THF (1 mL), was added, dropwise, a solution of the nitrile of Preparation 9, above, (85 mg, 0.181 mmol) in THF (0.5 mL). Upon completion of addition, the mixture was stirred for 15 additional minutes and then quenched by the sequential addition of H$_2$O (10 µL), 15% NaOH (10 µL), and H$_2$O (30 µL). The resulting slurry was stirred for an additional 45 minutes, then diluted 50 fold with EtOAc and filtered over a pad of diatomaceous earth. The filtrate was washed with saturated NaHCO$_3$ (aq), H$_2$O, and brine and concentrated under reduced pressure. The resulting residue was then purified by flash chromatography (SiO$_2$, 10% MeOH in CHCl$_3$ with 1% Et$_3$N added). To this amine (50 mg, 0.106 mmol) was added N-Boc-L-alanine (20 mg, 0.106 mmol), 1-(3-dimethylaminopropyl)-3-ethylcarbodiimide hydrochloride (41 mg, 0.212 mmol), a catalytic amount of 4-dimethylaminopyridine, and CH$_2$Cl$_2$ (1 mL). The mixture was stirred at room temperature for 45 minutes and then diluted 50 fold with EtOAc. The organics were washed with saturated NaHCO$_3$ (aq), H$_2$O, brine, and concentrated under reduced pressure. The material was purified by flash chromatography (SiO$_2$, 10% MeOH in CHCl$_3$); yielding 43 mg of the title compound.

$^1$H NMR (CDCl$_3$) δ 7.84 (d, J=6.7 Hz, 1H), 7.52 (d, J=7.0 Hz, 1H), 7.43 (d, J=8.6 Hz, 2H), 7.29 (m, 2H), 7.05 (d, J=8.5 Hz, 2H), 6.93 (d, J=8.7 Hz, 2H), 6.82 (d, J=8.4 Hz, 2H), 6.60 (bs, 1H), 4.95 (bs, 1H), 4.21 (s, 2H), 4.04–4.18 (m, 5H), 3.70 (dd, J=5.2, 10.4 Hz, 2H), 2.90 (t, J=5.8 Hz, 2H), 2.65 (s, 4H), 1.82 (s, 4H), 1.42 (s, 9H), 1.38 (d, J=7.1 Hz, 3H); FDMS 644.3 (M+1).

B. (S)-2-[4-[2-[(2-Amino-1-oxopropyl)amino]ethoxy]phenyl]-3-[4-[2-(1-pyrrolidinyl)ethoxy]benzylbenzo[b]thiophene Bis(trifluoroacetate).

The title compound was prepared in 81% yield from Example 8, Part A by essentially following the procedure outlined in Example 4, Part B.

$^1$H NMR (CD$_3$OD) δ 7.83 (d, J=7.1 Hz, 1H), 7.48 (d, J=7.6 Hz, 1H), 7.44 (d, J=8.6 Hz, 2H), 7.27 (m, 2H), 7.07 (d, J=8.5 Hz, 2H), 6.99 (d, J=8.7 Hz, 2H), 6.89 (d, J=8.6 Hz, 2H), 4.26 (t, J=5.1 Hz, 2H), 4.22 (s, 2H), 4.12 (t, J=5.2 Hz, 2H), 3.92 (m, 1H), 3.61–3.73 (m, 6H), 3.20 (m, 2H), 2.15 (bd, 4H), 1.48 (d, J=7.1 Hz, 3H); FAB MS 544.3 (M+1).

EXAMPLE 9

Preparation of (S)-2-[4-[2-[(2-Boc-amino-3-hydroxy-1-oxopropyl)amino]ethoxy]phenyl]-3-[4-[2-(1-pyrrolidinyl)ethoxy]benzylbenzo[b]thiophene

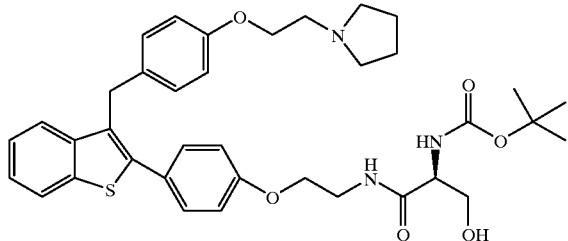

The titled compound was prepared in 56% yield from the nitrile of Preparation 9 and N-Boc-L-serine by essentially following the procedure outlined in Example 8, Part A.

$^1$H NMR (CDCl$_3$) δ 7.84 (d, J=6.7 Hz, 1H), 7.52 (d, J=6.7 Hz, 1H), 7.42 (d, J=8.6, 2H), 7.30 (m, 2H), 7.04 (d, J=8.5 Hz, 2H), 6.91 (d, J=8.6 Hz, 2H), 6.81 (d, J=8.6 Hz, 2H), 4.20 (s, 2H), 4.16 (m, 1H), 4.07 (m, 4H), 3.70 (m, 4H), 2.89 (t, J=6.0 Hz, 2H), 2.63 (s, 4H), 1.82 (s, 4H), 1.43 (s, 9H).

EXAMPLE 10

Preparation of (S)-2-[4-[(2-Amino-1-oxopropyl)amino]phenyl]-3-[4-[2-(1-pyrrolidinyl)ethoxy]benzylbenzo[b]thiophene Bis(trifluoroacetate)

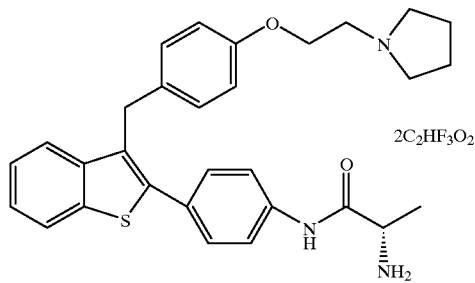

A. (S)-2-[4-[(2-Boc-amino-1-oxopropyl)amino]phenyl]-3-[4-[2-(1-pyrrolidinyl)ethoxy]benzylbenzo[b]thiophene.

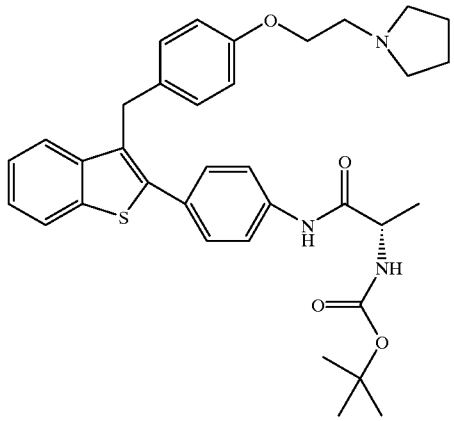

To the aniline (Preparation 5; 100 mg, 0.233 mmol) was added N-Boc-L-alanine (44 mg, 0.233), 1-(3-dimethylaminopropyl)-3-ethylcarbodiimide hydrochloride (89 mg, 0.466 mmol), a catalytic amount of 4-dimethylaminopyridine, and CH$_2$Cl$_2$ (1 mL). The mixture was stirred at room temperature, overnight, and then diluted 25 fold with EtOAc. The organics were washed with saturated NaHCO$_3$ (aq), H$_2$O, brine, and concentrated under reduced pressure. The material was then purified by flash chromatography (SiO$_2$, 10% MeOH in CHCl$_3$); yielding 127 mg (91%) of the title compound.

$^1$H NMR (CDCl$_3$) δ 7.78 (d, J=7.0 Hz, 1H), 7.54 (d, J=8.5 Hz, 2H), 7.49 (d, J=6.7 Hz, 1H), 7.46 (d, J=5.3 Hz, 2H), 7.30 (m, 2H), 7.00 (d, J=8.4 Hz, 2H), 6.79 (d, J=8.6 Hz, 2H), 4.41 (s, 1H), 4.14 (s, 2H), 4.06 (t, J=5.9 Hz, 2H), 2.89 (t, J=3.6 Hz, 2H), 2.64 (s, 4H), 1.82 (s, 4H), 1.48 (m, 12H); FDMS 599.2.

B. (S)-2-[4-[(2-Amino-1-oxopropyl)amino]phenyl]-3-[4-[2-(1-pyrrolidinyl)ethoxy]benzylbenzo[b]thiophene Bis(trifluoroacetate).

To the Boc-alanine compound (Example 10, Part A; 115 mg, 0.192 mmol) was added TFA (2 mL) and the solution allowed to stand at room temperature for 1 h. After concentrating under reduced pressure, the resulting residue was triturated with Et$_2$O and the off-white solid collected and dried; yielding 102 mg (73%) of the title compound.

$^1$H NMR (CD$_3$OD) δ 7.86 (d, J=8.3 Hz, 1H), 7.68 (d, J=8.4 Hz, 2H), 7.51 (m, 3H), 7.29 (m, 2H), 7.08 (d, J=8.6 Hz, 2H), 6.90 (d, J=8.6 Hz, 2H), 4.26 (m, 4H), 4.07 (m, 1H), 3.73 (m, 2H), 3.67 (t, J=1.2 Hz, 2H), 3.19 (m, 2H), 2.15 (bd, 4H), 1.60 (d, J=7.1 Hz, 3H); FAB MS 500.3 (M+1).

EXAMPLE 11

Preparation of (S)-2-[4-[4-[(2-Amino-1-oxopropyl)amino]butoxy]phenyl]-3-[4-[2-(1-pyrrolidinyl)ethoxy]benzylbenzo[b]thiophene Dihydrochloride

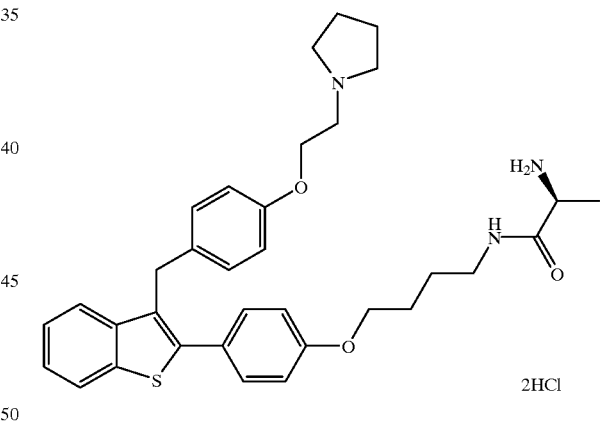

1-[2-[4-[[2-[4-(4-Aminobutoxy)phenyl]benzo[b]thiophen-3-yl]methyl]phenoxy]ethyl]pyrrolidine (Preparation 4; 51.8 mg, 0.103 mmol), N-(tert-butoxycarbonyl)-L-alanine (19.6 mg, 0.103 mmol, 1 eq), 1-(3-dimethylaminopropyl)-3-ethylcarbodiimide hydrochloride (40 mg, 0.207 mmol, 2 eq) and a catalytic amount of 4-(N,N-dimethylamino)pyridine were combined in just enough dry dichloromethane to permit stirring and the reaction was stirred at ambient temperature for about 1 h, until all starting amine was consumed, as determined by tlc (4:1 CHCl$_3$:MeOH). The reaction was diluted with ethyl acetate (50 mL) and water (50 mL) then the organic layer was separated and washed with brine (20 mL). The crude tert-butoxycarbonyl protected amino acid intermediate was passed through a plug of silica gel, eluting with (9:1 CHCl$_3$:MeOH). The semi-purified material was treated with excess TFA (1 mL) in dichloromethane (1 mL) for 30 min to remove the tert-butylcarbonyl group. The solvent was removed under reduced pressure then the residue purified by HPLC to give the desired product as a white solid (31 mg, 47% for two steps) after lypholization.

$^1$HNMR (300 MHz, CD$_3$OD) δ 7.82 (dd, J=8.6, 5.6 Hz, 1H), 7.51 (dd, J=8.6, 5.6 Hz, 1H), 7.42 (d, J=8.4 Hz, 2H), 7.32–7.20 (m, 2H), 7.11 (d, J=8.3 Hz, 2H), 6.98 (d, J=8.4 Hz, 2H), 6.89 (d, J=8.5 Hz, 2H), 4.28 (t, J=5.8 Hz, 2H), 4.20 (s, 2H), 4.08 (t, J=5.8 Hz, 2H), 3.92 (q, J=4.8 Hz, 1H), 3.72 (m, 2H), 3.61 (t J=5.8 Hz, 2H), 3.31 (m, 2H), 3.21 (m, 2H), 2.18 (bm, 2H), 2.05 (bm, 2H), 1.82 (bm, 2H), 1.75 (bm, 2H), 1.51 (d, J=4.8 Hz, 3H); FDMS m/e=572 (M+).

EXAMPLE 12

Preparation of (S)-2-[4-[(2-Boc-amino-3-methoxycarbonyl-1-oxopropyl)amino]phenyl]-3-[4-[2-(1-pyrrolidinyl)ethoxy]benzylbenzo[b]thiophene Hydrochloride

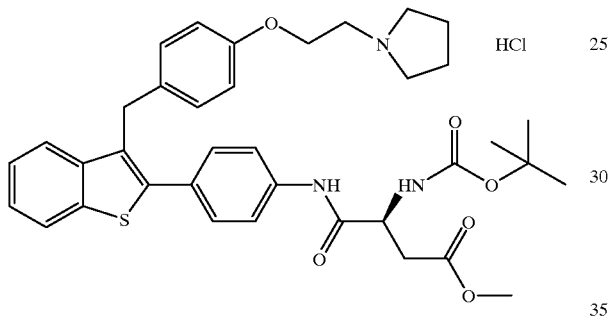

A. (S)-2-[4-[(2-Boc-Amino-3-methoxycarbonyl-1-oxopropyl)amino]phenyl]-3-[4-[2-(1-pyrrolidinyl)ethoxy]benzylbenzo[b]thiophene.

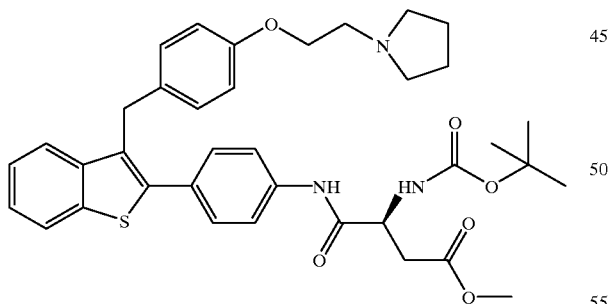

The compound was prepared from the aniline (Preparation 5; 80.2 mg, 0.187 mmol) in 88% yield by following essentially the same procedure as that for Example 11, except that the reaction required 18 h to go to completion and the intermediate tert-butoxycarbonyl protected amino acid derivative intermediate was purified by flash chromatography (silica gel, 20:1 CHCl$_3$:MeOH).

$^1$HNMR (300 MHz, CDCl$_3$) δ 8.80 (s, 1H), 7.84 (dd, J=6.0, 2.1 Hz, 1H), 7.56 (dd, J=6.0, 2.1 Hz, 1H), 7.54 (d, J=8.5 Hz, 2H), 7.45 (d, J=8.5 Hz, 2H), 7.32 7.23 (m, 2H), 7.04 (d, J=8.5 Hz, 2H), 6.80 (d, J=8.5 Hz, 2H), 5.98 (bs, 1H), 4.69 (bs, 1H), 4.21 (s, 2H), 4.08 (t, J=5.9 Hz, 2H), 3.74 (s, 3H), 2.82 (q, J=73.2, 17.0 Hz, 2H), 2.91 (t, J=5.9 Hz, 2H), 2.65 (bm, 4H), 1.82 (bm, 4H), 1.50 (s, 9H).

B. (S)-2-[4-[(2-Boc-amino-3-methoxycarbonyl-1-oxopropyl)amino]phenyl]-3-[4-[2-(1-pyrrolidinyl)ethoxy]benzylbenzo[b]thiophene Hydrochloride.

The title compound was prepared from the intermediate tert-butoxycarbonyl protected amino acid derivative (Part A, above, 21.6 mg, 0.0328 mmol) by treatment with dilute aqueous HCl (0.1 N) to give the desired product as a tan glass after lypholization (21.1 mg, 92%).

$^1$HNMR (300 MHz, CD$_3$OD) δ 9.95 (s, 1H), 7.83 (dd, J=6.8, 1.3 Hz, 1H), 7.55 (dd, J=6.8, 1.3 Hz, 1H), 7.61 (d, J=7.9 Hz, 2H), 7.50 (d, J=8.3 Hz, 2H), 7.43 (d, J=8.5 Hz, 2H), 7.32 7.23 (m, 2H), 7.05 (d, J=8.6 Hz, 2H), 6.87 (d, J=8.6 Hz, 2H), 4.60 (m, 1H), 4.25 (t, J=4.7 Hz, 2H), 4.20 (s, 2H), 3.68 (s, 3H), 3.60 (t, J=4.7 Hz, 2H), 3.21 (bm, 4H), 2.82 (q, J=49.4, 16.2 Hz, 2H), 2.15 (bm, 2H), 2.10 (bm, 2H), 1.45 (s, 9H); IR (CDCl$_3$) 2971, 1696, 1603, 1510, 1460, 1240, 1176 cm$^{-1}$; Anal. Cal'c for C$_{37}$H$_{44}$N$_3$O$_6$S.HCl.1.5 H$_2$O : C, 61.61 H, 6.57 N, 5.82 found: C, 61.62 H, 6.25 N, 5.77.

EXAMPLE 13

Preparation of (S)-2-[4-[(1-Boc-pyrrolidin-2-ylcarbonyl)amino]phenyl]-3-[4-[2-(1-pyrrolidinyl)ethoxy]benzylbenzo[b]thiophene

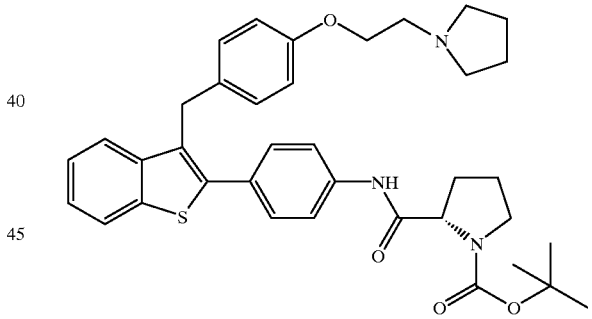

The compound was prepared from the aniline (Preparation 5; 83 mg, 0.19 mmol) in 77% yield by following essentially the same procedure as that for Example 11, above, except that the intermediate tert-butoxycarbonyl protected amino acid derivative intermediate was purified by flash chromatography (silica gel, 20:1 CHCl$_3$:MeOH).

$^1$HNMR (300 MHz, CDCl$_3$) δ 9.62 (bs, 1H), 7.82 (dd, J=8.7, 1.8 Hz, 1H), 7.55 (d, J=8.5 Hz, 2H), 7.50 (dd, J=0.87, 1.8 Hz, 1H), 7.43 (d, J=8.3 Hz, 2H), 7.32–7.24 (m, 2H), 7.03 (d, J=8.5 Hz, 2H), 6.80 (d, J=8.6 Hz, 2H), 4.48 (bm, 1H), 4.18 (s, 2H), 4.07 (t, J=6.0 Hz, 2H), 3.44 (bm, 1H), 2.89 (t, J=6.0 Hz, 2H), 263 (bm, 4H), 2.17 (bm, 1H), 1.94 (bm, 1H), 1.80 (bm, 4H), 1.50 (s, 9H).

EXAMPLE 14

Preparation of (S)-2-[4-[(2-Amino-3-methoxycarbonyl-1-oxopropyl)amino]phenyl]-3-[4-[2-(1-pyrrolidinyl)ethoxy]benzylbenzo[b]thiophene Dihydrochloride

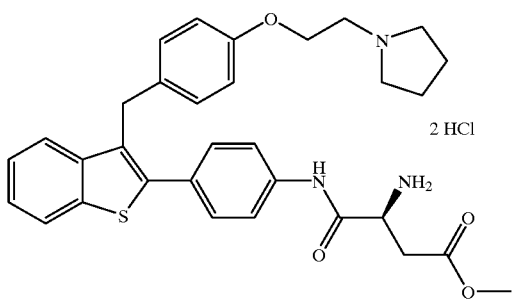

To a solution of the product of Example 12 (77 mg, 0.177 mmol) in dry dichloromethane (1 mL) was added trifluoroacetic acid (90 µL, 1.17 mmol, 10.0 eq.). When the starting material had been consumed, as indicated by tlc (silica, 9:1:0.1 chloroform:methanol:TEA), the solvents were removed under reduced pressure; then the residue was purified by preparative HPLC to give the title product as the hydrochloride salt (41 mg, 55%).

Analysis for $C_{32}H_{35}N_3O_4S \cdot 2HCl \cdot 2H_2O$: Calcd: C, 57.65; H, 6.20; N, 6.30; Found: C, 57.20; H, 5.93; N, 6.82.

EXAMPLE 15

Preparation of (S)-2-[4-[(2-Amino-1-oxo-3-phenylpropyl)amino]phenyl]-3-[4-[2-(1-pyrrolidinyl)ethoxy]benzylbenzo[b]thiophene Dihydrochloride

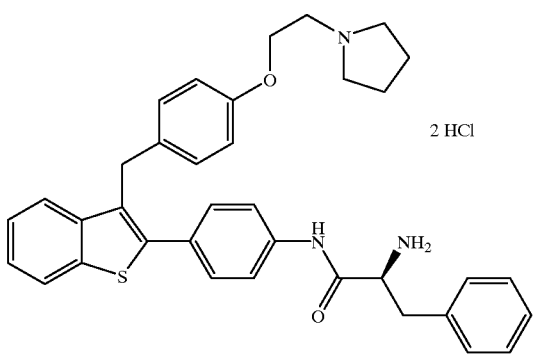

A. (S)-2-[4-[(2-Boc-amino-1-oxo-3-phenylpropyl)amino]phenyl]-3-[4-[2-(1-pyrrolidinyl)ethoxy]benzylbenzo[b]thiophene.

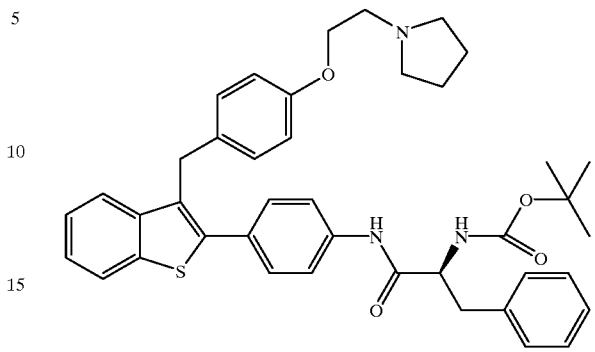

The compound was made essentially following the same procedure as for Example 12 above from the aniline (84 mg, 0.198 mmol) to give the title compound (98 mg, 74%).
FDMS (methanol) m/z=675.

B. (S)-2-[4-[(2-Amino-1-oxo-3-phenylpropyl)amino]phenyl]-3-[4-[2-(1-pyrrolidinyl)ethoxy]benzylbenzo[b]thiophene Dihydrochloride.

To a solution of the above urethane (56 mg, 0.083 mmol) in dichloromethane (1 mL) was added trifluoroacetic acid (64 µL, 0.832 mmol, 10 eq.); then the progress of the reaction was followed by tlc (9:1:0.1 chloroform:methanol:TEA). The solvents were then removed under reduced pressure and the residue purified by preparative HPLC to give the title product (19 mg, 35%).

FDMS (MeOH) m/z=576. Analysis for $C_{36}H_{37}N_3O_2S \cdot 2HCl \cdot 2H_2O$: Calcd: C, 63.25; H. 6.33; N, 6.14; Found: C, 63.12; H, 5.80; N, 5.69.

EXAMPLE 16

Preparation of (S)-2-[4-[(2-Amino-3-hydroxy-1-oxopropyl)amino]phenyl]-6-hydroxy-3-[3-methoxy-4-(1-pyrrolidinylmethyl)benzyl]benzo[b]thiophene Bis(trifluoroacetate)

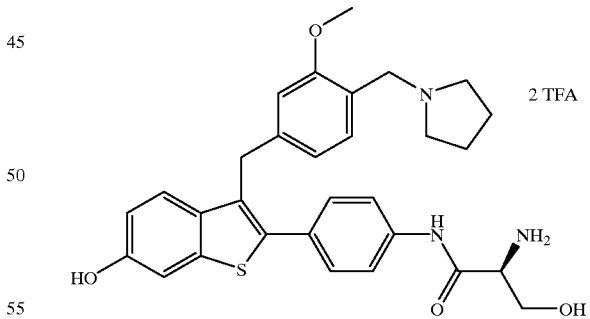

A. N-Boc-O-TBS-L-Serine.

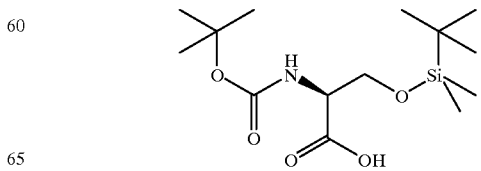

To a solution of N-tert-butoxycarbonyl-L-serine (1.4 g, 6.82 mmol) in dry dimethylformamide (7 mL) was added tertbutyldimethylsilyl chloride (2.3 g, 15.0 mmol, 2.2 eq) and imidazole (2.0 g, 30.0 mmol, 4.4 eq). After 18 h at ambient temperature, the reaction mixture was partitioned between hexanes (50 mL) and water (50 mL). The hexanes extract was washed with water (50 mL), dried (MgSO$_4$) and filtered; then the solvent was removed under reduced pressure to give a clear oil (2.75 g). The oil was taken up in methanol (70 mL) and THF (20 mL) then treated with aqueous potassium carbonate solution (10% w/v, 20 mL) for 1 h at ambient temperature. The volume of the reaction mixture was reduced to ⅓ the original under vacuum, then made acidic to pH 4.5 with aqueous potassium hydrogen sulfate (25% w/v). The resultant precipitate was extracted with ethyl acetate (3×25 mL). The combined extracts were dried (sodium sulfate), filtered, then concentrated under reduced pressure. The residual solvent was removed under vacuum (667 Pa) overnight. The resulting viscous oil (2.0 g) was used without further purification.

$^1$HNMR (300 MHz, CDCl$_3$) δ 0.37 (s, 3H), 0.44 (s, 3H), 0.85 (s, 9H), 1.43 (s, 9H), 3.93 (ABqt J=20, 8.0 Hz, 2H), 4.34 (t, J=3.6 Hz, 1H), 5.30 (d, J=8.0 Hz, 1H).

B. (S)-2-[4-[(2-Boc-amino-3-t-butyldimethylsilyloxy-1-oxopropyl)amino]phenyl]-6-benzyloxy-3-[3-methoxy-4-(1-pyrrolidinylmethyl)benzyl]benzo[b]thiophene.

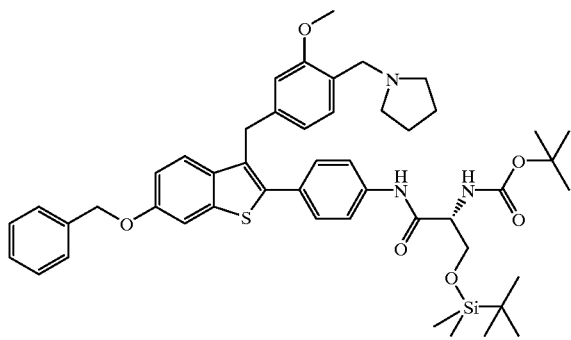

To a solution of the aniline (Preparation 7, 100 mg, 0.187 mmol) in dichloromethane (1 mL) was added the above silylated serine (60 mg, 0.187 mmol, 1.0 eq.), 1-(3-dimethylaminopropyl)-3-ethylcarbodiimide hydrochloride (72 mg, 0.374 mmol, 2.0 eq.) and a catalytic amount of 4-dimethylaminopyridine. The progress of the reaction was followed by tlc (9:1:0.1 chloroform:methanol:TEA). After 18 h, the reaction mixture was diluted 50-fold with ethyl acetate, washed with saturated sodium bicarbonate (25 mL), brine (25 mL), dried (sodium sulfate), and filtered. The solvents were then removed under reduced pressure and the residue purified by flash chromatography (silica, 5% methanol in chloroform) to give 124 mg (77%) of the indicated product.

$^1$HNMR (300 MHz, CDCl$_3$) δ 0.18 (s, 6H), 0.92 (s, 9H), 1.42 (s, 9H), 1.82 (bm, 4H), 2.81 (bm, 4H), 3.65 (s, 3H), 3.81 (s, 2H), 3.93 (ABqt, J=20, 8.0 Hz, 2H), 4.20 (s, 2H), 4.35 (t, J=4.3 Hz, 2H), 5.17 (s, 2H), 5.43 (d, J=8.0 Hz, 1H), 6.62 (s, 1H), 6.72 (d, J=7.8 Hz, 1H), 6.97 (d, J=7.9 Hz, 1H), 7.28–7.59 (m, 12 H).

C. (S)-2-[4-[(2-Boc-amino-3-hydroxy-1-oxopropyl)amino]phenyl]-6-benzyloxy-3-[3-methoxy-4-(1-pyrrolidinylmethyl)benzyl]benzo[b]thiophene.

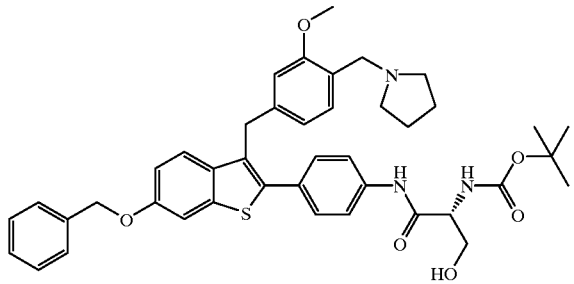

To a solution of the product of step B, above, (124 mg, 0.148 mmol) in wet THF (1 mL), was added a solution of tetrabutylammonium fluoride (163 μL of 1 M, 0.163 mmol, 1.1 eq) in THF at 0° C. The progress of the reaction was followed by tlc (4:1 chloroform:methanol). After 1 h, the reaction mixture was diluted 50-fold with ethyl acetate, washed with 5% aqueous sodium bicarbonate solution, dried (magnesium sulfate) and filtered. The solvent was removed under reduced pressure; then the residue was purified by flash chromatography (silica, 10% methanol in chloroform) to give the named product (90 mg, 84%).

$^1$HNMR (300 MHz, CDCl$_3$) δ 1.45 (s, 9H), 1.84 (bm, 4H), 2.76 (bm, 4H), 3.67 (s, 3H), 3.78 (s, 2H), 3.94 (ABqt, J=20, 8.0 Hz, 2H), 4.16 (s, 2H), 4.36 (t, J=4.3 Hz, 2H), 5.09 (s, 2H), 5.88 (d, J=8.0 Hz, 1H), 6.62 (s, 1H), 6.65 (d, J=7.6 Hz, 1H), 6.98 (d, J=7.6 Hz, 1H), 7.28–7.45 (m, 10 H) 7.54 (d, J=8.4 Hz, 2H), 9.15 (bs, 1H).

D. (S)-2-[4-[(2-Amino-3-hydroxy-1-oxopropyl)amino]phenyl]-6-hydroxy-3-[3-methoxy-4-(1-pyrrolidinylmethyl)benzyl]benzo[b]thiophene Bis(trifluoroacetate).

To a solution of the urethane of part C, above, (90 mg, 0.125 mmol) in methanol (2 mL) was added 5% Pd on carbon (90 mg, 1 wt. eq.) and ammonium formate (79 mg, 1.25 mmol, 10 eq.). The reaction mixture was heated at 60° C. with stirring for 10 min. The reaction mixture was cooled to ambient temperature, then filtered through a bed of diatomacous earth with methanol (50 mL) to remove the catalyst. The solvent was removed under reduced pressure; then the residue was taken up in ethyl acetate (50 mL) and washed with saturated aqueous sodium biacarbonate (25 mL) and water (25 mL); dried (magnesium sulfate) and filtered; then the solvent was removed under reduced pressure. The residue was treated with TFA (2 mL) at ambient temperature for 90 min. The excess TFA was removed under reduced pressure; then the residue was triturated with diethyl ether to give the title compound (86 mg, 90%) after drying under vacuum (667 Pa).

FDMS (methanol) m/z=532 (M+H).

EXAMPLE 17

Preparation of (R)-2-[4-[(3-Amino-4-hydroxy-1-oxobutyl)amino]phenyl]-6-hydroxy-3-[3-methoxy-4-(1-pyrrolidinylmethyl)benzyl]benzo[b]thiophene Bis(trifluoroacetate)

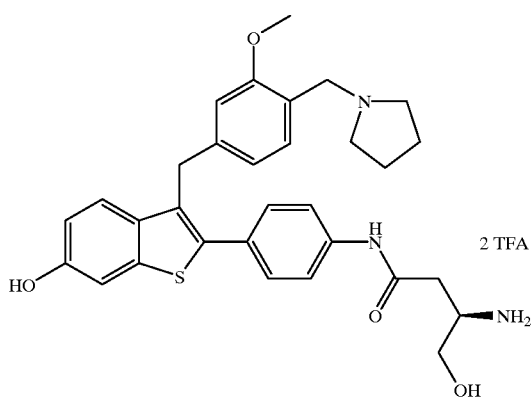

2 TFA

A. Benzyl (R)-3-Boc-amino-4-hydroxybutanoate.

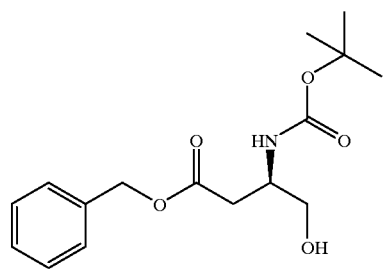

To a solution of N-tert-butoxycarbonyl-L-aspartic acid β-benzyl ester (2.03 g, 6.3 mmol) and N-methylmorpholine (690 μL, 6.3 mmol, 1.0 eq) in dry THF (30 mL) at −15° C. was added ethyl chloroformate (600 μL, 6.3 mmol, 1.0 eq), dropwise. After 10 min, the reaction was warmed to 0° C.; then sodium borohydride (713 mg, 18.8 mmol, 3.0 eq) was added in one portion. Methanol (63 mL) was added slowly, dropwise, over the course of 15 min. Once the evolution of gas from the reaction had ceased, the reaction was allowed to stir an additional 10 min; then 1N (aq) HCl (12.6 mL) was added. The solvents were removed under reduced pressure; then the residue was extracted with ethyl acetate (3×45 mL). The combined extracts were washed with IN HCl (45 mL), water (45 mL), 5% aq sodium bicarbonate and again with water (2×45 mL); dried (magnesium sulfate), filtered and concentrated under reduced pressure to a viscous oil. The oil was passed through a plug of silica, eluting with chloroform until the less polar impurities were removed, then 5% methanol in chloroform, to recover 1.5 g of the named product as a soft solid after removal of the solvent under reduced pressure.

$^1$HNMR (300 MHz, CDCl$_3$) δ 1.43 (s, 9H), 1.87 (bs, 1H), 2.62 (ABqt, J=60,8.1 Hz), 2.67 (d, J=6.1 Hz, 2H), 4.00 (m, 1H), 5.12 (s, 2H), 7.35 (m, 5H).

B. Benzyl (R)-3-Boc-amino-4-t-butyldimethyl-siyloxybutanoate.

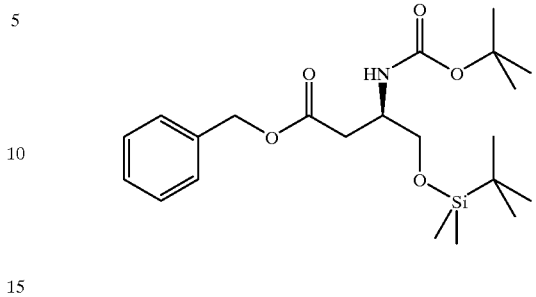

To a solution of the alcohol (1.3 g, 4.2 mmol), prepared above in part A, in dry DMF (4 mL), was added imidazole (572 mg, 8.4 mmol, 2.0 eq) and tert-butyldimethylsilyl chloride (633 mg, 4.2 mmol, 1.0 eq). After 18 h, the reaction mixture was partitioned between 1:1 hexanes:ethyl acetate (100 mL) and water (20 mL). The organic layer was washed with water (50 mL), dried (magnesium sulfate), filtered, and concentrated to a viscous oil under reduced pressure. The oil was passed through a plug of silica gel with 10% ethyl acetate in hexanes to give 1.22 g (67%) of the named product as a clear oil after removal of the solvent under reduced pressure.

$^1$HNMR (300 MHz, CDCl$_3$) δ 0.02 (s, 6H), 0.89 (s, 9H), 1.43 (s, 9H), 3.10 (ABqt, J=150, 8 Hz, 2H), 3.15 (ABqt, J=148, 8 Hz, 2H), 4.04 (m, 1H), 5.11 (s, 2H), 7.35 (m, 5H).

C. (R)-3-Boc-amino-4-t-butyldimethylsilyloxybutanoic Acid.

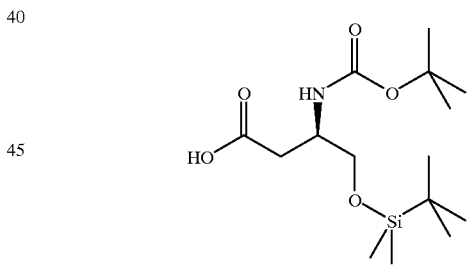

To a solution of the above protected amino acid (1.22 g, 2.88 mmol) in ethyl acetate (3 mL) was added 5% Pd on carbon (500 mg); then the reaction mixture was stirred vigorously under hydrogen for 2 h. The reaction mixture was filtered through a pad of diatomaecous earth with ethyl acetate (50 mL). The solvent was removed under reduced pressure; then the residue was dried overnight under vacuum (667 Pa). The crude oil (1.0 g, 104%) was used without further purification.

$^1$HNMR (300 MHz, CDCl$_3$) δ 0.51 (s, 6H), 0.89 (s, 9H), 1.44 (s, 9H), 2.63 (d, J=5.9 Hz, 2H), 3.67 (m, 2H), 4.02 (m, 1H), 5.10 (m, 1H).

D. (R)-2-[4-[(3-Boc-amino-4-t-butyldimethylsilyloxy-1-oxobutyl)amino]phenyl]-6-benzyloxy-3-[3-methoxy-4-(1-pyrrolidinylmethyl)benzyl]benzo[b]thiophene.

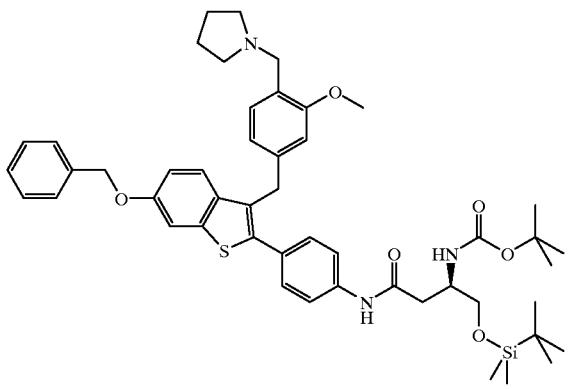

To a solution of the aniline (Preparation 7, 170 mg, 0.318 mmol) in dichloromethane (1 mL) was added the above protected amino acid (106 mg, 0.318 mmol, 1.0 eq), 1-(3-dimethylaminopropyl)-3-ethylcarbodiimide hydrochloride (122 mg 0.636 mmol, 2.0 eq), and a catalytic amount of 4-dimethylaminopyridine. After 3 h, the reaction mixture was diluted 50-fold with ethyl acetate and washed with saturated sodium bicarbonate (25 mL), then brine (25 mL). The solvent was removed under reduced pressure and the residue purified by chromatography (silica, 5% methanol in chloroform) to give 219 mg (81%) of the indicated product.

Analysis for $C_{49}H_{63}N_3O_6SSi$: Calcd: C, 69.22; H, 7.46; N, 4.94; Found C: 69.11; H, 7.25; N, 5.03.

E. (R)-2-[4-[(3-Boc-amino-4-hydroxy-1-oxobutyl)amino]-phenyl]-6-benzyloxy-3-[3-methoxy-4-(1-pyrrolidinylmethyl)benzyl]benzo[b]thiophene.

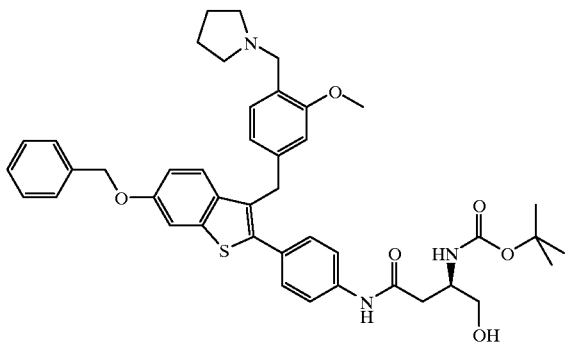

To a solution of the product of part D (200 mg, 235 mmol) in THF (1 mL) was added a solution of tetrabutylammonium fluoride (282 μL of 1M, 0.282 mmol, 1.1 eq) in THF at 0° C. The reaction was allowed to warm to ambient temperature after 15 min, then stir for 30 min at ambient temperature. The reaction was diluted 50-fold with ethyl acetate; then washed with 5% aqueous sodium bicarbonate (15 mL), water (2×15 mL) and brine (25 mL). The organic layer was dried (magnesium sulfate), filtered and concentrated to a foam uunder reduced pressure. The crude foam was purified by chromatography (silica, 5–10% methanol in chloroform) to give 160 mg (92%) of the indicated product.

Analysis for $C_{43}H_{49}N_3O_6S$: Calcd: C, 70.18; H, 6.71; N, 5.71; Found: C: 69.90; H, 6.58; N, 5.66.

F. (R)-2-[4-[(3-Amino-4-hydroxy-1-oxobutyl)amino] phenyl]-6-hydroxy-3-[3-methoxy-4-(1-pyrrolidinylmethyl) benzyl]benzo[b]thiophene Bis(trifluoroacetate).

To a solution of the benzyl ether prepared above (110 mg, 0.149 mmol) in methanol (1 mL), was added 5% Pd on carbon (110 mg, 1 wt eq) and ammonium formate (94 mg, 1.49 mmol, 10 eq). The reaction mixture was heated at reflux for 10 min, then cooled to ambient temperature. The catalyst was removed via filtration through a pad of diatomacous earth with methanol (50 mL). The solvent was removed under reduced pressure then the residue taken up in TFA (1 mL) for 1 h. The TFA was removed under reduced pressure and the residue triturated with diethyl ether to give the title compound (99 mg, 86%) as a brown solid.

Analysis for $C_{31}H_{35}N_3O_4S \cdot 2TFA$: Calcd: C, 54.33; H, 4.82; N, 5.34; Found: C, 54.54; H, 5.06; N, 5.36.

EXAMPLE 18

Preparation of (S)-2-[4-[(2-Amino-3-benzyloxy-1-oxopropyl)amino]phenyl]-3-[4-[2-(1-pyrrolidinyl)ethoxy]benzylbenzo[b]thiophene Bis (trifluoroacetate)

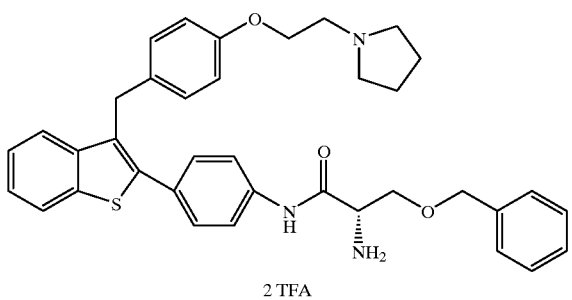

To 86 mg (0.200 mmol) of the aniline (Preparation 5, Part D), in $CH_2Cl_2$ (1 mL), was added N-Boc-O-benzyl-L-serine (59 mg, 0.200 mL), 1-(3-dimethylaminopropyl)-3-ethylcarbodiimide hydrochloride (77 mg, 0.400 mmol), and a catalytic amount of 4-dimethylaminopyridine. The mixture was stirred at room temperature overnight then diluted 50 fold with EtOAc. The organics were washed with saturated $NaHCO_3$, $H_2O$, brine, and concentrated, in vacuo. Material was purified by flash chromatography ($SiO_2$, 5% MeOH in $CHCl_3$) and the resulting product subjected to TFA (2 mL) deprotection. The salt was triturated with $Et_2O$ and dried; yielding 31 mg of title product.

FAB MS 606.4 (M+). Analysis for $C_{37}H_{39}N_3O_3S \cdot 2 C_2HF_3O_2 \cdot 1.1 H_2O$: Calcd: C, 57.68; H, 5.10; N, 4.92; Found: C, 57.38; H, 4.85; N, 5.14.

EXAMPLE 19

Preparation of (S)-2-[4-[(1-Pyrrolidin-2-ylcarbonyl)amino]phenyl]-3-[4-[2-(1-pyrrolidinyl)ethoxy]benzylbenzo[b]thiophene Bis(trifluoroacetate)

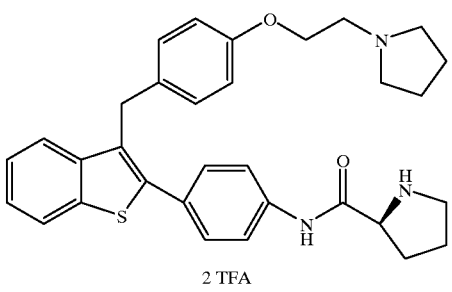

To 83 mg (0.194 mmol) of the aniline (Preparation 5, Part D), in $CH_2Cl_2$ (1 mL), was added N-Boc-L-proline (42 mg, 0.194 mL), 1-(3-dimethylaminopropyl)-3-ethylcarbodiimide hydrochloride (74 mg, 0.388 mmol), and a catalytic amount of 4-dimethylaminopyridine. The mixture was stirred at room temperature overnight then diluted 50 fold with EtOAc. The organics were washed with saturated NaHCO$_3$, H$_2$O, brine, and concentrated, in vacuo. Material was purified by flash chromatography (SiO$_2$, 5% MeOH in CHCl$_3$) and the resulting product subjected to TFA (2 mL) deprotection. The salt was triturated with Et$_2$O and dried.

$^1$H NMR (CD$_3$OD) δ 7.86 (d, J=8.2 Hz, 1H), 7.68 (d, J=8.5 Hz, 2H), 7.52 (m, 3H), 7.32 (m, 2H), 7.07 (d, J=8.6 Hz, 2H), 6.91 (d, J=8.6 Hz, 2H), 4.41 (m 1H), 4.25 (m, 4H), 3.72 (m, 2H), 3.61 (t, J=4.9 Hz, 2H), 3.45 (m, 2H), 3.20 (m, 2H), 2.55 (m, 2H), 2.02–2.19 (m, 6H); FAB MS 526.3 (M+1).

What is claimed is:

1. A compound of formula I, or a pharmaceutically acceptable salt thereof,

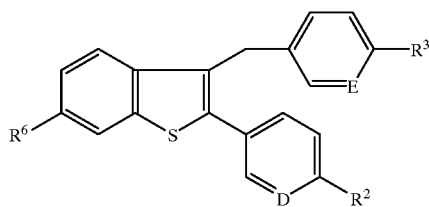

I wherein

D is CH, CR$^d$ or N in which R$^d$ is methyl or methoxy;

E is CH, CR$^e$ or N in which R$^e$ is methyl, methoxy or halo;

R$^2$ is —{X$^2$—(CH$_2$)$_n$}$_p$—N(R$^a$)—CO—A in which X$^2$ is a direct bond, methylene or O; n is 1, 2, 3 or 4; p is 0 or 1, R$^a$ is hydrogen or methyl; and —CO—A is an α-amino acyl group derived from an α-amino acid selected from glycine, alanine, valine, leucine, isoleucine, phenylalanine, tyrosine, serine, threonine, methionine, cysteine, proline, azetidine-2-carboxylic acid, pipecolic acid, aspartic acid, asparginine, glutamic acid, glutamine, lysine, arginine or histidine in which an amino group may bear a t-butoxy carbonyl protecting group; a carboxy group may be protected as its (1–4C)alkyl ester; a hydroxy group may bear a benzyl protecting group; and a thiol group may bear a t-butyl protecting group; or —CO—A is represented as —CO—CH(R$^b$)—NR$^f$R$^g$, each of R$^f$ and R$^g$ is hydrogen or methyl, or —NR$^f$R$^g$ is a pyrrolidino, piperidino, morpholine or 1,1-dioxo thiomorpholin-4-yl group (and R$^b$ denotes the side chain or protected side chain of an α-amino acyl group as defined hereinabove), provided that p is 1 when —CO—A is a glycyl or N-substituted glycyl group; or —CO—A is 3-amino-4-hydroxy-1-oxobutyl;

R$^3$ is —X$^3$—(CH$_2$)$_s$—NR$^s$R$^t$ or —CH$_2$—R$^k$, in which X$^3$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and R$^k$ is 2-oxopyrrolidin-1-yl or 3-(1-oxoethyl) imidazolidin-1-yl; and R$^6$ is hydrogen, hydroxy or methoxy.

2. The compound of formula I, or a pharmaceutically acceptable salt thereof, as claimed in claim 1 wherein D is CH, CR$^d$ or N in which R$^d$ is methyl or methoxy;

E is CH, CR$^e$ or N in which R$^e$ is methyl, methoxy or halo;

R$^2$ is —{X$^2$—(CH$_2$)$_n$}$_p$—N(R$^a$)—CO—A in which X$^2$ is a direct bond, methylene or O; n is 1, 2, 3 or 4; p is 0 or 1, R$^a$ is hydrogen or methyl; and —CO—A is an α-amino acyl group derived from an α-amino acid selected from glycine, alanine, valine, leucine, isoleucine, phenylalanine, tyrosine, serine, threonine, methionine, cysteine, proline, azetidine-2-carboxylic acid, pipecolic acid, aspartic acid, asparginine, glutamic acid, glutamine, lysine, arginine or histidine in which an amino group may bear a t-butoxycarbonyl protecting group; a carboxy group may be protected as its (1–4C)alkyl ester; a hydroxy group may bear a benzyl protecting group; and a thiol group may bear a t-butyl protecting group; or —CO—A is represented as —CO—CH(R$^b$)—NR$^f$R$^g$, each of R$^f$ and R$^g$ is hydrogen or methyl, or —NR$^f$R$^g$ is a pyrrolidino, piperidino, morpholine or 1,1-dioxothiomorpholin-4-yl group (and R$^b$ denotes the side chain or protected side chain of an α-amino acyl group as defined hereinabove), provided that p is 1 when —CO—A is a glycyl or N-substituted glycyl group;

R$^3$ is —X$^3$—(CH$_2$)$_s$—NR$^s$R$^t$ or —CH$_2$—R$^k$, in which X$^3$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and R$^k$ is 2-oxopyrrolidin-1-yl or 3-(1-oxoethyl) imidazolidin-1-yl; and R$^6$ is hydrogen, hydroxy or methoxy.

3. The compound, or salt thereof, as claimed in claim 1 wherein, independently, D is CH; and E is CH or CR$^e$ in which R$^e$ is methoxy.

4. The compound, or salt thereof, as claimed in claim 1 wherein R$^3$ is pyrrolidinomethyl or 2-pyrrolidinoethoxy.

5. The compound, or salt thereof, as claimed in claim 1 wherein —CO—A is O-benzyl-L-serinyl, L-serinyl, N-(t-butoxycarbonyl)-L-serinyl, L-aspartyl, L-phenylalanyl, L-alanyl, L-tyrosinyl, L-asparaginyl, N-(t-butoxycarbonyl)-γ-methyl-L-glutamyl or N-(t-butoxycarbonyl)-L-prolinyl.

6. The compound, or salt thereof, as claimed in claim 1 wherein —CO—A is (R)-3-amino-4-hydroxy-1-oxobutyl.

7. The compound, or salt thereof, as claimed in claim 1 wherein R$^6$ is hydroxy.

8. The compound, or salt thereof, as claimed in claim 1 wherein p is 1; X$^2$ is O; and n is 2, 3 or 4.

9. The compound, or salt thereof, as claimed in claim 1 wherein p is 0.

10. The compound, or salt thereof, as claimed in claim 1 or 2 wherein halo is fluoro, chloro, bromo or iodo; a (1–3C)alkyl group is methyl, ethyl, propyl or isopropyl; and a (1–4C)alkyl group is methyl, ethyl, propyl, isopropyl or t-butyl.

11. The compound of claim 1 which is (S)-2-[4-[(2-amino-3-hydroxy-1-oxopropyl)amino]phenyl]-6-hydroxy-3-[3-methoxy-4-(1-pyrrolidinylmethyl)benzyl]benzo[b]thiophene, or a pharmaceutically acceptable salt thereof.

12. The compound of claim 1 which is (R)-2-[4-[(3-amino-4-hydroxy-1-oxobutyl)amino]phenyl]-6-hydroxy-3-[3-methoxy-4-(1-pyrrolidinylmethyl)benzyl]benzo[b]thiophene, or a pharmaceutically acceptable salt thereof.

13. The pharmaceutically acceptable salt of claim 1 which is an acid-addition salt made with an acid which provides a pharmaceutically acceptable anion or which is the salt made with a base which provides a pharmaceutically acceptable cation.

14. A pharmaceutical formulation comprising in association with a pharmaceutically acceptable carrier, diluent or excipient, a compound of formula I, or a pharmaceutically acceptable salt thereof, as provided in claim 1.

15. A process for preparing a compound of formula I, or a pharmaceutically acceptable salt thereof, as claimed in claim 1 which is acylation of the amino group of a corresponding amine of formula II;

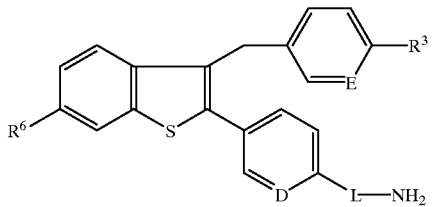

II wherein L is —{$X^2$—(CH$_2$)$_n$}$_p$— with an acid of formula HO—CO—A, or an activated derivative thereof;
whereafter when a functional group is protected using a protecting group, removing the protecting group;
whereafter when a pharmaceutically acceptable salt of a compound of formula I is required, reacting the basic or acidic form of such a compound of formula I with an acid or base affording a physiologically acceptable counterion or by any other conventional procedure;
and wherein D, E, $R^2$, $R^3$ and $R^6$ have the values described in claim 1.

16. The compound, or salt thereof, as claimed in claim 2 wherein, independently, D is CH; and E is CH or CR$^e$ in which R$^e$ is methoxy.

17. The compound, or salt thereof, as claimed in claim 2 wherein $R^3$ is pyrroldinomethyl or 2-pyrrolidinoethoxy.

18. The compound, or salt thereof, as claimed in claim 3 wherein $R^3$ is pyrroldinomethyl or 2-pyrrolidinoethoxy.

19. The compound, or salt thereof, as claimed in claim 2 wherein —CO—A is O-benzyl-L-serinyl, L-serinyl, N-(t-butoxycarbonyl)-L-serinyl, L-aspartyl, L-phenylalanyl, L-alanyl, L-tyrosinyl, L-asparaginyl, N-(t-butoxycarbonyl)-γ-methyl-L-glutamyl or N-(t-butoxycarbonyl-L-prolinyl.

20. The compound, or salt thereof, as claimed in claim 3 wherein —CO—A is O-benzyl-L-serinyl, L-serinyl, N-(t-butoxycarbonyl)-L-serinyl, L-aspartyl, L-phenylalanyl, L-alanyl, L-tyrosinyl, L-asparaginyl, N-(t-butoxycarbonyl)-γ-methyl-L-glutamyl or N-(t-butoxycarbonyl-L-prolinyl.

21. The compound, or salt thereof, as claimed in claim 4 wherein —CO—A is O-benzyl-L-serinyl, L-serinyl, N-(t-butoxycarbonyl)-L-serinyl, L-aspartyl, L-phenylalanyl, L-alanyl, L-tyrosinyl, L-asparaginyl, N-(t-butoxycarbonyl)-γ-methyl-L-glutamyl or N-(t-butoxycarbonyl-L-prolinyl.

22. The compound, or salt thereof, as claimed in claim 2 wherein —CO—A is (R)-3-amino-4-hydroxy-1-oxobutyl.

23. The compound, or salt thereof, as claimed in claim 3 wherein —CO—A is (R)-3-amino-4-hydroxy-1-oxobutyl.

24. The compound, or salt thereof, as claimed in claim 4 wherein —CO—A is (R)-3-amino-4-hydroxy-1-oxobutyl.

25. The compound, or salt thereof, as claimed in claim 2 wherein $R^6$ is hydroxy.

26. The compound, or salt thereof, as claimed in claim 3 wherein $R^6$ is hydroxy.

27. The compound, or salt thereof, as claimed in claim 4 wherein $R^6$ is hydroxy.

28. The compound, or salt thereof, as claimed in claim 5 wherein $R^6$ is hydroxy.

29. The compound, or salt thereof, as claimed in claim 6 wherein $R^6$ is hydroxy.

30. The compound, or salt thereof, as claimed in claim 2 wherein p is 1; $X^2$ is O; and n is 2, 3, or 4.

31. The compound, or salt thereof, as claimed in claim 3 wherein p is 1; $X^2$ is O; and n is 2, 3, or 4.

32. The compound, or salt thereof, as claimed in claim 4 wherein p is 1; $X^2$ is O; and n is 2, 3, or 4.

33. The compound, or salt thereof, as claimed in claim 5 wherein p is 1; $X^2$ is O; and n is 2, 3, or 4.

34. The compound, or salt thereof, as claimed in claim 6 wherein p is 1; $X^2$ is O; and n is 2, 3, or 4.

35. The compound, or salt thereof, as claimed in claim 7 wherein p is 1; $X^2$ is O; and n is 2, 3, or 4.

36. The compound, or salt thereof, as claimed in claim 2 wherein p is 0.

37. The compound, or salt thereof, as claimed in claim 3 wherein p is 0.

38. The compound, or salt thereof, as claimed in claim 4 wherein p is 0.

39. The compound, or salt thereof, as claimed in claim 5 wherein p is 0.

40. The compound, or salt thereof, as claimed in claim 6 wherein p is 0.

41. The compound, or salt thereof, as claimed in claim 7 wherein p is 0.

42. A method of inhibiting thrombin in a patient comprising administering to the patient in need thereof a thrombin inhibiting amount of a compound of claim 1 or a pharmaceutically acceptable salt thereof.

* * * * *